United States Patent [19]

Choiu et al.

[11] Patent Number: 6,025,178
[45] Date of Patent: Feb. 15, 2000

[54] HUMAN PHOSPHOLIPASE $A_2$ AND RELATED NUCLEIC ACID COMPOUNDS

[75] Inventors: Xue-Chiou C. Choiu, Lake Bluff, Ill.; Ruth M. Kramer, Indianapolis, Ind.; Richard T. Pickard, Noblesville, Ind.; John D. Sharp, Indianapolis, Ind.; Beth A. Strifler, Brownsburg, Ind.

[73] Assignee: Eli Lilly and Company, Indianapolis, Ind.

[21] Appl. No.: 08/827,208

[22] Filed: Mar. 28, 1997

Related U.S. Application Data

[60] Provisional application No. 60/014,608, Mar. 29, 1996.

[51] Int. Cl.[7] ................... C12N 9/20; C12N 1/20; C12P 21/06; C07H 21/04

[52] U.S. Cl. ..................... 435/198; 435/69.1; 435/252.3; 435/320.1; 536/23.2; 530/350

[58] Field of Search ..................... 435/198, 69.1, 435/252.3, 320.1, 369; 536/23.2; 530/350

[56] References Cited

U.S. PATENT DOCUMENTS 5,622,832  4/1997  Knopf et al. ............................... 435/19

*Primary Examiner*—Ponnathapu Achutamurthy
*Assistant Examiner*—Tekchand Saidha
*Attorney, Agent, or Firm*—Paul J. Gaylo

[57] ABSTRACT

The invention provides a novel phospholipase $A_2$ enzyme, polynucleotides encoding such enzyme and methods for screening unknown compounds for anti-inflammatory activity mediated by the arachidonic acid cascade.

1 Claim, No Drawings

HUMAN PHOSPHOLIPASE A₂ AND RELATED NUCLEIC ACID COMPOUNDS

PRIORITY CLAIM

This application claims the priority of U.S. Provisional Patent Applications No. 60/014,608, filed Mar. 29, 1996 and Attorney Docket Number X-10610B, filed Mar 19, 1997.

BACKGROUND OF THE INVENTION

Inflammatory and degenerative disorders account for a significant number of debilitating diseases. Inflammatory states, such as arthritis, psoriasis, asthma, and possibly atherosclerosis, stem from inflammatory reactions in the joints, skin, and blood vessels. It is generally believed that a central role in the inflammatory reaction is the production of phospholipid metabolites called eicosanoids. The eicosanoids represent a family of important mediators such as the leukotrienes, prostaglandins, lipoxins, hydroxyeicosatetreanoic acid, and thromboxanes. It is believed that the generation of eicosanoids is dependent on the availability of arachidonic acid which is liberated from phospholipids by the action of phospholipase $A_2$ (EC 3.1.1.4).

Phospholipase $A_2$ (PLA$_2$) is the common name for phosphatide 2-acylhydrolase, which catalyzes the hydrolysis of the sn-2-acyl ester bond of phosphoglycerides which results in the production of equimolar amounts of lysophospholipids and free fatty acids. see, E. A. Dennis, THE ENZYMES, Vol. 16, Academic Press, New York, (1983). Phospholipase $A_2$ enzymes are found in all living species and form a diverse family of enzymes. Over eighty phospholipase $A_2$ enzymes have been structurally characterized, and they show a high degree of sequence homology. J. Chang, et al., *Biochemical Pharmacology*, 36:2429–2436, (1987); F. F. Davidson and E. A. Dennis, *Journal of Molecular Evolution*, 31:228–238 (1990).

The best characterized varieties of PLA$_2$ enzyme are the secreted forms, which are released into the extracellular environment where they aid in the digestion of biological materials. The secreted forms have a molecular weight of about 12–15,000 (Davidson and Dennis, supra). In contrast, cytosolic phospholipases $A_2$ are found in small amounts within the cell and play a key role in the biosynthetic pathway leading to the formation of the platelet activating factors and the eicosanoids. R. M. Kramer, SIGNAL-ACTIVATED PHOSPHOLIPASES, (M. Liscontdi, ed. 1994) pp. 13–30; J. D. Sharp, et al., *Journal of Biological Chemistry*, 266:14850–14853 (1991).

The cytosolic phospholipases $A_2$ have a molecular weight of approximately 85,000 daltons. J. D. Clark, et al., *Cell*, 65:1043–1051 (1991). Free arachidonic acid is the rate limiting precursor for the production of eicosanoids and is liberated from its membrane phospholipid store by the action of cytosolic PLA$_2$. E. A. Dennis, *Drug Development and Research*, 10:205–220, (1987). The same enzymatic step also produces lysophospholipids which may be converted to platelet-activating factors. Thus, it is believed that cytosolic PLA$_2$ is central to the regulation of the biosynthetic pathways of potent lipid mediators of inflammation.

Recent studies have begun to indicate that a major component of the pathology of Alzheimer's disease is chronic inflammation. See, J. Schnabel, *Science*, 260:1719–1720 (1993). Indeed, pathological investigations have demonstrated the presence of glial hyperactivity, acute phase proteins, and complement factors within affected areas of the brains of persons affected with Alzheimer's disease. Administration of nonsteroidal anti-inflammatory drugs appears to slow the advance of Alzheimer's disease. Id. Understanding this inflammatory component of Alzheimer's disease, therefore, will lead to advances in novel methods of treating patients suffering from this disease.

Due to the central role in the inflammatory component of Alzheimer's disease that appears to be played by cytosolic phospholipase $A_2$, it is desirable to identify and characterize new inhibitors of this enzyme. The present invention provides a novel phospholipase $A_2$, nucleic acids encoding this enzyme, and assays which may be employed to identify inhibitors having a therapeutic benefit.

SUMMARY OF THE INVENTION

This invention provides an isolated amino acid compound useful as a phospholipase $A_2$, said compound comprising the amino acid sequence

```
Met Met Pro Ala Glu Arg Arg Leu Pro Leu Ser Phe Val Leu Asp Val
 1               5                  10                 15

Leu Glu Gly Arg Ala Gln His Pro Gly Val Leu Tyr Val Gln Lys Gln
             20                  25                 30

Cys Ser Asn Leu Pro Ser Glu Leu Pro Gln Leu Leu Pro Asp Leu Glu
             35                  40                 45

Ser His Val Pro Trp Ala Ser Glu Ala Leu Gly Lys Met Pro Asp Ala
         50                  55                 60

Val Asn Phe Trp Leu Gly Glu Ala Ala Val Thr Ser Leu His Lys
 65                  70                  75              80

Asp His Tyr Glu Asn Leu Tyr Cys Val Val Ser Gly Glu Lys His Phe
                     85                  90                 95

Leu Phe His Pro Pro Ser Asp Arg Pro Phe Ile Pro Tyr Glu Leu Tyr
                 100                 105                110

Thr Pro Ala Thr Tyr Gln Leu Thr Glu Glu Gly Thr Phe Lys Val Val
             115                 120                 125

Asp Glu Glu Ala Met Glu Lys Ala Glu Val Ser Arg Thr Cys Leu Leu
```

```
            130                 135                 140
Thr Val Arg Val Leu Gln Ala His Arg Leu Pro Ser Lys Asp Leu Val
145                 150                 155                 160

Thr Pro Ser Asp Cys Tyr Val Thr Leu Trp Leu Pro Thr Ala Cys Ser
                165                 170                 175

His Arg Leu Gln Thr Arg Thr Val Lys Asn Ser Ser Ser Ser Val Trp
                180                 185                 190

Asn Gln Ser Phe His Phe Arg Ile His Arg Gln Leu Lys Asn Val Met
                195                 200                 205

Glu Leu Lys Val Phe Asp Gln Asp Leu Val Thr Gly Asp Asp Pro Val
            210                 215                 220

Leu Ser Val Leu Phe Asp Ala Gly Thr Leu Arg Ala Gly Glu Phe Arg
225                 230                 235                 240

Arg Glu Ser Phe Ser Leu Ser Pro Gln Gly Glu Gly Arg Leu Glu Val
                245                 250                 255

Glu Phe Arg Leu Gln Ser Leu Ala Asp Arg Gly Glu Trp Leu Val Ser
                260                 265                 270

Asn Gly Val Leu Val Ala Arg Glu Leu Ser Cys Leu His Val Gln Leu
            275                 280                 285

Glu Glu Thr Gly Asp Gln Lys Ser Ser Glu His Arg Val Gln Leu Val
            290                 295                 300

Val Pro Gly Ser Cys Glu Gly Pro Gln Glu Ala Ser Val Gly Thr Gly
305                 310                 315                 320

Thr Phe Arg Phe His Cys Pro Ala Cys Trp Glu Gln Glu Leu Ser Ile
                325                 330                 335

Arg Leu Gln Asp Ala Pro Glu Glu Gln Leu Lys Ala Pro Leu Ser Ala
                340                 345                 350

Leu Pro Ser Gly Gln Val Val Arg Leu Val Phe Pro Thr Ser Gln Glu
                355                 360                 365

Pro Leu Met Arg Val Glu Leu Lys Lys Glu Ala Gly Leu Arg Glu Leu
            370                 375                 380

Ala Val Arg Leu Gly Phe Gly Pro Cys Ala Glu Glu Gln Ala Phe Leu
385                 390                 395                 400

Ser Arg Arg Lys Gln Val Val Ala Ala Ala Leu Arg Gln Ala Leu Gln
                405                 410                 415

Leu Asp Gly Asp Leu Gln Glu Asp Glu Ile Pro Val Val Ala Ile Met
                420                 425                 430

Ala Thr Gly Gly Gly Ile Arg Ala Met Thr Ser Leu Tyr Gly Gln Leu
            435                 440                 445

Ala Gly Leu Lys Glu Leu Gly Leu Leu Asp Cys Val Ser Tyr Ile Thr
            450                 455                 460

Gly Ala Ser Gly Ser Thr Trp Ala Leu Ala Asn Leu Tyr Glu Asp Pro
465                 470                 475                 480

Glu Trp Ser Gln Lys Asp Leu Ala Gly Pro Thr Glu Leu Leu Lys Thr
                485                 490                 495

Gln Val Thr Lys Asn Lys Leu Gly Val Leu Ala Pro Ser Gln Leu Gln
                500                 505                 510

Arg Tyr Arg Gln Glu Leu Ala Glu Arg Ala Arg Leu Gly Tyr Pro Ser
                515                 520                 525

Cys Phe Thr Asn Leu Trp Ala Leu Ile Asn Glu Ala Leu Leu His Asp
                530                 535                 540

Glu Pro His Asp His Lys Leu Ser Asp Gln Arg Glu Ala Leu Ser His
545                 550                 555                 560
```

-continued

```
Gly Gln Asn Pro Leu Pro Ile Tyr Cys Ala Leu Asn Thr Lys Gly Gln
            565                 570                 575
Ser Leu Thr Thr Phe Glu Phe Gly Glu Trp Cys Glu Phe Ser Pro Tyr
            580                 585                 590
Glu Val Gly Phe Pro Lys Tyr Gly Ala Phe Ile Pro Ser Glu Leu Phe
            595                 600                 605
Gly Ser Glu Phe Phe Met Gly Gln Leu Met Lys Arg Leu Pro Glu Ser
            610                 615                 620
Arg Ile Cys Phe Leu Glu Gly Ile Trp Ser Asn Leu Tyr Ala Ala Asn
625                 630                 635
Leu Gln Asp Ser Leu Tyr Trp Ala Ser Glu Pro Ser Gln Phe Trp Asp
            645                 650                 655
Arg Trp Val Arg Asn Gln Ala Asn Leu Asp Lys Glu Gln Val Pro Leu
            660                 665                 670
Leu Lys Ile Glu Glu Pro Pro Ser Thr Ala Gly Arg Ile Ala Glu Phe
            675                 680                 685
Phe Thr Asp Leu Leu Thr Trp Arg Pro Leu Ala Gln Ala Thr His Asn
            690                 695                 700
Phe Leu Arg Gly Leu His Phe His Lys Asp Tyr Phe Gln His Pro His
705                 710                 715                 720
Phe Ser Thr Trp Lys Ala Thr Thr Leu Asp Gly Leu Pro Asn Gln Leu
            725                 730                 735
Thr Pro Ser Glu Pro His Leu Cys Leu Leu Asp Val Gly Tyr Leu Ile
            740                 745                 750
Asn Thr Ser Cys Leu Pro Leu Leu Gln Pro Thr Arg Asp Val Asp Leu
            755                 760                 765
Ile Leu Ser Leu Asp Tyr Asn Leu His Gly Ala Phe Gln Gln Leu Gln
            770                 775                 780
Leu Leu Gly Arg Phe Cys Gln Glu Gln Gly Ile Pro Phe Pro Pro Ile
785                 790                 795                 800
Ser Pro Ser Pro Glu Glu Gln Leu Gln Pro Arg Glu Cys His Thr Phe
            805                 810                 815
Ser Asp Pro Thr Cys Pro Gly Ala Pro Ala Val Leu His Phe Pro Leu
            820                 825                 830
Val Ser Asp Ser Phe Arg Glu Tyr Ser Ala Pro Gly Val Arg Arg Thr
            835                 840                 845
Pro Glu Glu Ala Ala Ala Gly Glu Val Asn Leu Ser Ser Ser Asp Ser
            850                 855                 860
Pro Tyr His Tyr Thr Lys Val Thr Tyr Ser Gln Glu Asp Val Asp Lys
865                 870                 875                 880
Leu Leu His Leu Thr His Tyr Asn Val Cys Asn Asn Gln Glu Gln Leu
            885                 890                 895
Leu Glu Ala Leu Arg Gln Ala Val Gln Arg Arg Gln Arg Arg Pro
            900                 905                 910
His
``` hereinafter referred to as SEQ ID NO:3, and having activity as a phospholipase A$_2$. This phospholipase A$_2$ is alternatively referred to as bPLA$_2$ or PLA$_2$-beta.

The invention also provides an isolated nucleic acid compound that comprises a nucleic acid sequence which encodes the amino acid compounds provided. Particularly this invention provides the isolated nucleic acid compound having the sequence

| | |
|---|---|
| CCGTGACCCC AGATGGTTAC GCGGATGCCG TGAGAGGGGA TCGCTTC ATG ATG CCA<br>                                               Met Met Pro<br>                                                1 | 56 |
| GCT GAG CGC CGC CTG CCC CTG AGC TTC GTG CTG GAT GTG CTG GAG GGC<br>Ala Glu Arg Arg Leu Pro Leu Ser Phe Val Leu Asp Val Leu Glu Gly<br>    5          10          15 | 104 |
| CGC GCC CAG CAC CCT GGA GTC CTC TAT GTG CAG AAG CAG TGC TCC AAC<br>Arg Ala Gln His Pro Gly Val Leu Tyr Val Gln Lys Gln Cys Ser Asn<br>20          25          30         35 | 152 |
| CTG CCC AGC GAG CTG CCC CAG CTG CTG CCT GAT CTG GAA TCC CAT GTG<br>Leu Pro Ser Glu Leu Pro Gln Leu Leu Pro Asp Leu Glu Ser His Val<br>        40          45         50 | 200 |
| CCC TGG GCC TCC GAA GCC CTG GGA AAG ATG CCC GAT GCT GTG AAC TTC<br>Pro Trp Ala Ser Glu Ala Leu Gly Lys Met Pro Asp Ala Val Asn Phe<br>      55          60         65 | 248 |
| TGG CTG GGG GAG GCG GCT GCA GTG ACT TCT TTG CAC AAG GAC CAC TAT<br>Trp Leu Gly Glu Ala Ala Ala Val Thr Ser Leu His Lys Asp His Tyr<br>    70          75         80 | 296 |
| GAG AAC CTC TAC TGC GTG GTC TCA GGA GAG AAG CAT TTC CTG TTC CAT<br>Glu Asn Leu Tyr Cys Val Val Ser Gly Glu Lys His Phe Leu Phe His<br>  85         90         95 | 344 |
| CCG CCC AGC GAC CGG CCC TTC ATC CCC TAT GAG CTG TAC ACG CCG GCA<br>Pro Pro Ser Asp Arg Pro Phe Ile Pro Tyr Glu Leu Tyr Thr Pro Ala<br>100         105         110        115 | 392 |
| ACC TAC CAG CTA ACT GAA GAG GGC ACC TTT AAG GTG GTG GAT GAA GAG<br>Thr Tyr Gln Leu Thr Glu Glu Gly Thr Phe Lys Val Val Asp Glu Glu<br>         120         125        130 | 440 |
| GCC ATG GAG AAG GCA GAG GTG TCC AGG ACC TGC CTG CTC ACG GTT CGT<br>Ala Met Glu Lys Ala Glu Val Ser Arg Thr Cys Leu Leu Thr Val Arg<br>      135          140         145 | 488 |
| GTC CTG CAG GCC CAT CGC CTA CCC TCT AAG GAC CTA GTG ACC CCC TCT<br>Val Leu Gln Ala His Arg Leu Pro Ser Lys Asp Leu Val Thr Pro Ser<br>    150          155         160 | 536 |
| GAC TGC TAC GTG ACT CTC TGG CTG CCC ACG GCC TGC AGC CAC AGG CTC<br>Asp Cys Tyr Val Thr Leu Trp Leu Pro Thr Ala Cys Ser His Arg Leu<br>  165         170         175 | 584 |
| CAG ACA CGC ACG GTC AAG AAC AGC AGT AGC TCT GTC TGG AAC CAG AGC<br>Gln Thr Arg Thr Val Lys Asn Ser Ser Ser Ser Val Trp Asn Gln Ser<br>180         185         190        195 | 632 |
| TTT CAC TTC AGG ATC CAC AGG CAG CTC AAG AAT GTC ATG GAA CTG AAA<br>Phe His Phe Arg Ile His Arg Gln Leu Lys Asn Val Met Glu Leu Lys<br>         200         205        210 | 680 |
| GTC TTT GAC CAG GAC CTG GTG ACC GGA GAT GAC CCT GTG TTG TCA GTA<br>Val Phe Asp Gln Asp Leu Val Thr Gly Asp Asp Pro Val Leu Ser Val<br>      215          220        225 | 728 |
| CTG TTT GAT GCG GGG ACT CTG CGG GCT GGG GAG TTC CGG CGC GAG AGC<br>Leu Phe Asp Ala Gly Thr Leu Arg Ala Gly Glu Phe Arg Arg Glu Ser<br>    230         235        240 | 776 |
| TTC TCA CTG AGC CCT CAG GGT GAG GGG CGC CTG GAA GTT GAA TTT CGC<br>Phe Ser Leu Ser Pro Gln Gly Glu Gly Arg Leu Glu Val Glu Phe Arg<br>  245         250        255 | 824 |
| CTG CAG AGT CTG GCT GAC CGT GGC GAG TGG CTC GTC AGC AAT GGC GTT<br>Leu Gln Ser Leu Ala Asp Arg Gly Glu Trp Leu Val Ser Asn Gly Val<br>260         265         270        275 | 872 |
| CTG GTG GCC CGG GAG CTC TCC TGC TTG CAC GTT CAA CTG GAG GAG ACA<br>Leu Val Ala Arg Glu Leu Ser Cys Leu His Val Gln Leu Glu Glu Thr<br>      280          285        290 | 920 |
| GGA GAC CAG AAG TCC TCA GAG CAC AGA GTT CAG CTT GTG GTT CCT GGG<br>Gly Asp Gln Lys Ser Ser Glu His Arg Val Gln Leu Val Val Pro Gly | 968 |

-continued

|     |     |     | 295 |     |     |     |     | 300 |     |     |     |     | 305 |     |     |      |
|-----|-----|-----|-----|-----|-----|-----|-----|-----|-----|-----|-----|-----|-----|-----|-----|------|
| TCC | TGT | GAG | GGT | CCG | CAG | GAG | GCC | TCT | GTG | GGC | ACT | GGC | ACC | TTC | CGC | 1016 |
| Ser | Cys | Glu | Gly | Pro | Gln | Glu | Ala | Ser | Val | Gly | Thr | Gly | Thr | Phe | Arg |      |
|     |     | 310 |     |     |     |     | 315 |     |     |     |     | 320 |     |     |     |      |

| TTC | CAC | TGC | CCA | GCC | TGC | TGG | GAG | CAG | GAG | CTG | AGT | ATT | CGC | CTG | CAG | 1064 |
|-----|-----|-----|-----|-----|-----|-----|-----|-----|-----|-----|-----|-----|-----|-----|-----|------|
| Phe | His | Cys | Pro | Ala | Cys | Trp | Glu | Gln | Glu | Leu | Ser | Ile | Arg | Leu | Gln |      |
|     |     | 325 |     |     |     |     | 330 |     |     |     |     | 335 |     |     |     |      |

| GAT | GCC | CCC | GAG | GAG | CAA | CTA | AAG | GCG | CCA | CTG | AGT | GCC | CTG | CCC | TCT | 1112 |
|-----|-----|-----|-----|-----|-----|-----|-----|-----|-----|-----|-----|-----|-----|-----|-----|------|
| Asp | Ala | Pro | Glu | Glu | Gln | Leu | Lys | Ala | Pro | Leu | Ser | Ala | Leu | Pro | Ser |      |
| 340 |     |     |     |     | 345 |     |     |     |     | 350 |     |     |     |     | 355 |      |

| GGT | CAA | GTG | GTG | AGG | CTT | GTC | TTC | CCC | ACG | TCC | CAG | GAG | CCC | CTG | ATG | 1160 |
|-----|-----|-----|-----|-----|-----|-----|-----|-----|-----|-----|-----|-----|-----|-----|-----|------|
| Gly | Gln | Val | Val | Arg | Leu | Val | Phe | Pro | Thr | Ser | Gln | Glu | Pro | Leu | Met |      |
|     |     |     |     | 360 |     |     |     |     | 365 |     |     |     |     | 370 |     |      |

| AGA | GTG | GAG | CTG | AAA | AAA | GAA | GCA | GGA | CTG | AGG | GAG | CTG | GCC | GTG | CGA | 1208 |
|-----|-----|-----|-----|-----|-----|-----|-----|-----|-----|-----|-----|-----|-----|-----|-----|------|
| Arg | Val | Glu | Leu | Lys | Lys | Glu | Ala | Gly | Leu | Arg | Glu | Leu | Ala | Val | Arg |      |
|     |     |     | 375 |     |     |     |     | 380 |     |     |     |     | 385 |     |     |      |

| CTG | GGC | TTC | GGG | CCC | TGT | GCA | GAG | GAG | CAG | GCC | TTC | CTG | AGC | AGG | AGG | 1256 |
|-----|-----|-----|-----|-----|-----|-----|-----|-----|-----|-----|-----|-----|-----|-----|-----|------|
| Leu | Gly | Phe | Gly | Pro | Cys | Ala | Glu | Glu | Gln | Ala | Phe | Leu | Ser | Arg | Arg |      |
|     |     |     | 390 |     |     |     |     | 395 |     |     |     |     | 400 |     |     |      |

| AAG | CAG | GTG | GTG | GCC | GCG | GCC | TTG | AGG | CAG | GCC | CTG | CAG | CTG | GAT | GGA | 1304 |
|-----|-----|-----|-----|-----|-----|-----|-----|-----|-----|-----|-----|-----|-----|-----|-----|------|
| Lys | Gln | Val | Val | Ala | Ala | Ala | Leu | Arg | Gln | Ala | Leu | Gln | Leu | Asp | Gly |      |
|     |     | 405 |     |     |     |     | 410 |     |     |     |     | 415 |     |     |     |      |

| GAC | CTG | CAG | GAG | GAT | GAG | ATC | CCA | GTG | GTA | GCT | ATT | ATG | GCC | ACT | GGT | 1352 |
|-----|-----|-----|-----|-----|-----|-----|-----|-----|-----|-----|-----|-----|-----|-----|-----|------|
| Asp | Leu | Gln | Glu | Asp | Glu | Ile | Pro | Val | Val | Ala | Ile | Met | Ala | Thr | Gly |      |
| 420 |     |     |     |     | 425 |     |     |     |     | 430 |     |     |     |     | 435 |      |

| GGT | GGG | ATC | CGG | GCA | ATG | ACT | TCC | CTG | TAT | GGG | CAG | CTG | GCT | GGC | CTG | 1400 |
|-----|-----|-----|-----|-----|-----|-----|-----|-----|-----|-----|-----|-----|-----|-----|-----|------|
| Gly | Gly | Ile | Arg | Ala | Met | Thr | Ser | Leu | Tyr | Gly | Gln | Leu | Ala | Gly | Leu |      |
|     |     |     |     | 440 |     |     |     |     | 445 |     |     |     |     | 450 |     |      |

| AAG | GAG | CTG | GGC | CTC | TTG | GAT | TGC | GTC | TCC | TAC | ATC | ACC | GGG | GCC | TCG | 1448 |
|-----|-----|-----|-----|-----|-----|-----|-----|-----|-----|-----|-----|-----|-----|-----|-----|------|
| Lys | Glu | Leu | Gly | Leu | Leu | Asp | Cys | Val | Ser | Tyr | Ile | Thr | Gly | Ala | Ser |      |
|     |     |     | 455 |     |     |     |     | 460 |     |     |     |     | 465 |     |     |      |

| GGC | TCC | ACC | TGG | GCC | TTG | GCC | AAC | CTT | TAT | GAG | GAC | CCA | GAG | TGG | TCT | 1496 |
|-----|-----|-----|-----|-----|-----|-----|-----|-----|-----|-----|-----|-----|-----|-----|-----|------|
| Gly | Ser | Thr | Trp | Ala | Leu | Ala | Asn | Leu | Tyr | Glu | Asp | Pro | Glu | Trp | Ser |      |
|     |     | 470 |     |     |     |     | 475 |     |     |     |     | 480 |     |     |     |      |

| CAG | AAG | GAC | CTG | GCA | GGG | CCC | ACT | GAG | TTG | CTG | AAG | ACC | CAG | GTG | ACC | 1544 |
|-----|-----|-----|-----|-----|-----|-----|-----|-----|-----|-----|-----|-----|-----|-----|-----|------|
| Gln | Lys | Asp | Leu | Ala | Gly | Pro | Thr | Glu | Leu | Leu | Lys | Thr | Gln | Val | Thr |      |
|     | 485 |     |     |     |     | 490 |     |     |     |     | 495 |     |     |     |     |      |

| AAG | AAC | AAG | CTG | GGT | GTG | CTG | GCC | CCC | AGC | CAG | CTG | CAG | CGG | TAC | CGG | 1592 |
|-----|-----|-----|-----|-----|-----|-----|-----|-----|-----|-----|-----|-----|-----|-----|-----|------|
| Lys | Asn | Lys | Leu | Gly | Val | Leu | Ala | Pro | Ser | Gln | Leu | Gln | Arg | Tyr | Arg |      |
| 500 |     |     |     |     | 505 |     |     |     |     | 510 |     |     |     |     | 515 |      |

| CAG | GAG | CTG | GCC | GAG | CGT | GCC | CGC | TTG | GGC | TAC | CCA | AGC | TGC | TTC | ACC | 1640 |
|-----|-----|-----|-----|-----|-----|-----|-----|-----|-----|-----|-----|-----|-----|-----|-----|------|
| Gln | Glu | Leu | Ala | Glu | Arg | Ala | Arg | Leu | Gly | Tyr | Pro | Ser | Cys | Phe | Thr |      |
|     |     |     |     | 520 |     |     |     |     | 525 |     |     |     |     | 530 |     |      |

| AAC | CTG | TGG | GCC | CTC | ATC | AAC | GAG | GCG | CTG | CTG | CAT | GAT | GAG | CCC | CAT | 1688 |
|-----|-----|-----|-----|-----|-----|-----|-----|-----|-----|-----|-----|-----|-----|-----|-----|------|
| Asn | Leu | Trp | Ala | Leu | Ile | Asn | Glu | Ala | Leu | Leu | His | Asp | Glu | Pro | His |      |
|     |     |     | 535 |     |     |     |     | 540 |     |     |     |     | 545 |     |     |      |

| GAT | CAC | AAG | CTC | TCA | GAT | CAA | CGG | GAG | GCC | CTG | AGT | CAT | GGC | CAG | AAC | 1736 |
|-----|-----|-----|-----|-----|-----|-----|-----|-----|-----|-----|-----|-----|-----|-----|-----|------|
| Asp | His | Lys | Leu | Ser | Asp | Gln | Arg | Glu | Ala | Leu | Ser | His | Gly | Gln | Asn |      |
|     |     | 550 |     |     |     |     | 555 |     |     |     |     | 560 |     |     |     |      |

| CCT | CTG | CCC | ATC | TAC | TGT | GCC | CTC | AAC | ACC | AAA | GGG | CAG | AGC | CTG | ACC | 1784 |
|-----|-----|-----|-----|-----|-----|-----|-----|-----|-----|-----|-----|-----|-----|-----|-----|------|
| Pro | Leu | Pro | Ile | Tyr | Cys | Ala | Leu | Asn | Thr | Lys | Gly | Gln | Ser | Leu | Thr |      |
|     | 565 |     |     |     |     | 570 |     |     |     |     | 575 |     |     |     |     |      |

| ACT | TTT | GAA | TTT | GGG | GAG | TGG | TGC | GAG | TTC | TCT | CCC | TAC | GAG | GTC | GGC | 1832 |
|-----|-----|-----|-----|-----|-----|-----|-----|-----|-----|-----|-----|-----|-----|-----|-----|------|
| Thr | Phe | Glu | Phe | Gly | Glu | Trp | Cys | Glu | Phe | Ser | Pro | Tyr | Glu | Val | Gly |      |
| 580 |     |     |     |     | 585 |     |     |     |     | 590 |     |     |     |     | 595 |      |

| TTC | CCC | AAG | TAC | GGG | GCC | TTC | ATC | CCC | TCT | GAG | CTC | TTT | GGC | TCC | GAG | 1880 |
|-----|-----|-----|-----|-----|-----|-----|-----|-----|-----|-----|-----|-----|-----|-----|-----|------|
| Phe | Pro | Lys | Tyr | Gly | Ala | Phe | Ile | Pro | Ser | Glu | Leu | Phe | Gly | Ser | Glu |      |
|     |     |     |     | 600 |     |     |     |     | 605 |     |     |     |     | 610 |     |      |

| TTC | TTT | ATG | GGG | CAG | CTG | ATG | AAG | AGG | CTT | CCT | GAG | TCC | CGC | ATC | TGC | 1928 |

-continued

```
                Phe Phe Met Gly Gln Leu Met Lys Arg Leu Pro Glu Ser Arg Ile Cys
                            615                 620                 625

TTC TTA GAA GGT ATC TGG AGC AAC CTG TAT GCA GCC AAC CTC CAG GAC          1976
Phe Leu Glu Gly Ile Trp Ser Asn Leu Tyr Ala Ala Asn Leu Gln Asp
            630                 635                 640

AGC TTA TAC TGG GCC TCA GAG CCC AGC CAG TTC TGG GAC CGC TGG GTC          2024
Ser Leu Tyr Trp Ala Ser Glu Pro Ser Gln Phe Trp Asp Arg Trp Val
            645                 650                 655

AGG AAC CAG GCC AAC CTG GAC AAG GAG CAG GTC CCC CTT CTG AAG ATA          2072
Arg Asn Gln Ala Asn Leu Asp Lys Glu Gln Val Pro Leu Leu Lys Ile
660                 665                 670                 675

GAA GAA CCA CCC TCA ACA GCC GGC AGA ATA GCT GAG TTT TTC ACC GAT          2120
Glu Glu Pro Pro Ser Thr Ala Gly Arg Ile Ala Glu Phe Phe Thr Asp
                680                 685                 690

CTT CTG ACG TGG CGT CCA CTG GCC CAG GCC ACA CAT AAT TTC CTG CGT          2168
Leu Leu Thr Trp Arg Pro Leu Ala Gln Ala Thr His Asn Phe Leu Arg
            695                 700                 705

GGC CTC CAT TTC CAC AAA GAC TAC TTT CAG CAT CCT CAC TTC TCC ACA          2216
Gly Leu His Phe His Lys Asp Tyr Phe Gln His Pro His Phe Ser Thr
            710                 715                 720

TGG AAA GCT ACC ACT CTG GAT GGG CTC CCC AAC CAG CTG ACA CCC TCG          2264
Trp Lys Ala Thr Thr Leu Asp Gly Leu Pro Asn Gln Leu Thr Pro Ser
    725                 730                 735

GAG CCC CAC CTG TGC CTG CTG GAT GTT GGC TAC CTC ATC AAT ACC AGC          2312
Glu Pro His Leu Cys Leu Leu Asp Val Gly Tyr Leu Ile Asn Thr Ser
740                 745                 750

TGC CTG CCC CTC CTG CAG CCC ACT CGG GAC GTG GAC CTC ATC CTG TCA          2360
Cys Leu Pro Leu Leu Gln Pro Thr Arg Asp Val Asp Leu Ile Leu Ser
                760                 765                 770

TTG GAC TAC AAC CTC CAC GGA GCC TTC CAG CAG TTG CAG CTC CTG GGC          2408
Leu Asp Tyr Asn Leu His Gly Ala Phe Gln Gln Leu Gln Leu Leu Gly
            775                 780                 785

CGG TTC TGC CAG GAG CAG GGG ATC CCG TTC CCA CCC ATC TCG CCC AGC          2456
Arg Phe Cys Gln Glu Gln Gly Ile Pro Phe Pro Pro Ile Ser Pro Ser
            790                 795                 800

CCC GAA GAG CAG CTC CAG CCT CGG GAG TGC CAC ACC TTC TCC GAC CCC          2504
Pro Glu Glu Gln Leu Gln Pro Arg Glu Cys His Thr Phe Ser Asp Pro
    805                 810                 815

ACC TGC CCC GGA GCC CCT GCG GTG CTG CAC TTT CCT CTG GTC AGC GAC          2552
Thr Cys Pro Gly Ala Pro Ala Val Leu His Phe Pro Leu Val Ser Asp
820                 825                 830                 835

TCC TTC CGG GAG TAC TCG GCC CCT GGG GTC CGG CGG ACA CCC GAG GAG          2600
Ser Phe Arg Glu Tyr Ser Ala Pro Gly Val Arg Arg Thr Pro Glu Glu
                840                 845                 850

GCG GCA GCT GGG GAG GTG AAC CTG TCT TCA TCG GAC TCT CCC TAC CAC          2648
Ala Ala Ala Gly Glu Val Asn Leu Ser Ser Ser Asp Ser Pro Tyr His
            855                 860                 865

TAC ACG AAG GTG ACC TAC AGC CAG GAG GAC GTG GAC AAG CTG CTG CAC          2696
Tyr Thr Lys Val Thr Tyr Ser Gln Glu Asp Val Asp Lys Leu Leu His
            870                 875                 880

CTG ACA CAT TAC AAT GTC TGC AAC AAC CAG GAG CAG CTG CTG GAG GCT          2744
Leu Thr His Tyr Asn Val Cys Asn Asn Gln Glu Gln Leu Leu Glu Ala
    885                 890                 895

CTG CGC CAG GCA GTG CAG CGG AGG CGG CAG CGC AGG CCC CAC                  2786
Leu Arg Gln Ala Val Gln Arg Arg Arg Gln Arg Arg Pro His
900                 905                 910

TGATGGCCGG GGCCCCTGCC ACCCCTAACT CTCATTCATT CCCTGGCTGC TGAGTTGCAG        2846

GTGGGAACTG TCATCACGCA GTGCTTCAGA GCCTCGGGCT CAGGTGGCAC TGTCCCAGGG        2906
```

```
                                   -continued

TCCAGGCTGA  GGGCTGGGAG  CTCCCTTGCG  CCTCAGCAGT  TTGCAGTGGG  GTAAGGAGGC    2966

CAAGCCCATT  TGTGTAATCA  CCCAAAACCC  CCCGGCCTGT  GCCTGTTTTC  CCTTCTGCGC    3026

TACCTTGAGT  AGTTGGAGCA  CTTGATACAT  CACAGACTCA  TACAAAAAAA  AAAAAAAAAA    3085
``` hereinafter referred to as SEQ ID NO:2.

The present invention also provides processes for producing a phospholipase enzyme, said process comprising: (a) establishing a culture of the host cell transformed with a bPLA$_2$ encoding polynucleotide in a suitable culture medium; and (b) isolating said enzyme from said culture. Compositions comprising a peptide made according to such processes are also provided.

The present invention also provides methods for identifying an inhibitor of phospholipase activity, said method comprising: (a) combining a phospholipid, a candidate inhibitor compound, and a composition comprising a protein of the present invention; and (b) observing whether said protein of the present invention cleaves said phospholipid and releases fatty acid thereby. Inhibitors of phospholipase activity identified by such methods, pharmaceutical compositions comprising a therapeutically effective amount of such inhibitors and a pharmaceutically acceptable carrier, and methods of reducing inflammation by administering such pharmaceutical compositions to a mammalian subject are also provided.

Polyclonal and monoclonal antibodies to the peptides of the invention are also provided.

DETAILED DESCRIPTION AND PREFERRED EMBODIMENTS

The terms and abbreviations used in this document have their normal meanings unless otherwise designated. For example "_C" refers to degrees Celsius; "N" refers to normal or normality; "mmol" refers to millimole or millimoles; "g" refers to gram or grams; "ml" means milliliter or milliliters; "M" refers to molar or molarity; "µg" refers to microgram or micrograms; and "µl" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenosine, (deoxy)cytidine, (deoxy)guanosine, and (deoxy)thymidine, respectively, when they occur in DNA molecules. The abbreviations U,C,G, and A correspond to the 5'-monophosphate forms of the ribonucleosides uridine, cytidine, guanosine, and adenosine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. To insure against improper translation, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter to control transcription of the inserted DNA has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., MOLECULAR CLONING: A LABORATORY MANUAL, (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refer to pairs of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two completely or nearly completely complementary nucleic acid strands varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO: 1, a sequence complementary to SEQ ID NO: 1, or a part thereof.

The term "stringency" refers to a set of hybridization conditions which may be varied in order to vary the degree of nucleic acid affinity for other nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other phospholipase $A_2$ variants. This term may also be employed in the sense that such antibodies may be used to differentiate between the human phospholipase $A_2$ protein and analogous proteins derived from other species.

The term "PCR" as used herein refers to the widely-known polymerase chain reaction employing a thermally-stable polymerase.

The phospholipase $A_2$ enzymes comprise a widely distributed family of enzymes which catalyze the hydrolysis of the acyl ester bond of glycerophospholipids at the sn-2 position. One kind of phospholipase $A_2$ enzymes, secreted phospholipase $A_2$, or "14 kD secreted sPLA$_2$", are involved in a number of biological functions, including phospholipid digestion, the toxic activities of numerous venoms, and potential antibacterial activities. A second kind of phospholipase $A_2$ enzymes, the intracellular phospholipase $A_2$ enzymes, also known as cytosolic phospholipase $A_2$ or cPLA$_2$, are active in membrane phospholipid turnover and in regulation of intracellular signaling mediated by the multiple components of the well-known arachidonic acid cascade. One or more cPLA$_2$ enzymes are believed to be responsible for the rate limiting step in the arachidonic acid cascade, namely, release of arachidonic acid from membrane glycerophospholipids. The action of cPLA$_2$ also results in biosynthesis of platelet activating factor (PAF).

The phospholipase B enzymes are a family of enzymes which catalyze the hydrolysis of the acyl ester bond of glycerophospholipids at the sn-1 and sn-2 positions. The mechanism of hydrolysis is unclear but may consist of initial hydrolysis of the sn-2 fatty acid followed by rapid cleavage of the sn-1 substituent, i.e., functionally equivalent to the combination of phospholipase $A_2$ and lysophospholipase (Salto, et al., *Methods of Enzymology*, 1991, 197:446; Gassama-Diagne, et al., *Journal of Biological Chemistry*, 1989, 264:9470). Whether these two events occur at the same or two distinct active sites has not been resolved. It is also unknown if these enzymes have a preference for the removal of unsaturated fatty acids, in particular arachidonic acid, at the sn-2 position and, accordingly, contribute to the arachidonic acid cascade.

Upon release from the membrane, arachidonic acid may be metabolized via the cyclooxygenase pathway to produce the various prostaglandins and thromboxanes, or via the lipoxygenase pathway to produce the various leukotrienes and related compounds. The prostaglandins, leukotrienes and platelet activating factor are well known mediators of various inflammatory states, and numerous anti-inflammatory drugs have been developed which function by inhibiting one or more steps in the arachidonic acid cascade. Use of the present anti-inflammatory drugs which act through inhibition of arachidonic acid cascade steps has been limited by the existence of side effects which may be harmful to various individuals.

A very large industrial effort has been made to identify additional anti-inflammatory drugs which inhibit the arachidonic acid cascade. In general, this industrial effort has employed the secreted phospholipase $A_2$ enzymes in inhibitor screening assays, for example, as disclosed in U.S. Pat. No. 4,917,826. However, because the secreted phospholipase $A_2$ enzymes are extracellular proteins (i.e., not cytosolic) and are not specific for hydrolysis of arachidonic acid, they are presently not believed to participate directly in the arachidonic acid cascade. While some inhibitors of the small secreted phospholipase $A_2$ enzymes have anti-inflammatory action, such as indomethacin, bromphenacyl bromide, mepacrine, and certain butyrophenones as disclosed in U.S. Pat. No. 4,239,780, it is presently believed that inhibitor screening assays should employ cytosolic phospholipase $A_2$ enzymes which directly participate in the arachidonic acid cascade.

An improvement in the search for anti-inflammatory drugs which inhibit the arachidonic acid cascade was developed in commonly assigned U.S. Pat. No. 5,322,776, incorporated herein by reference. In that application, a cytosolic form of phospholipase $A_2$ was identified, isolated, and cloned. Use of the cytosolic form of phospholipase $A_2$ to screen for anti-inflammatory drugs provides a significant improvement in identifying inhibitors of the arachidonic acid cascade. The cytosolic phospholipase $A_2$ disclosed in U.S. Pat. No. 5,322,776 is an 85 kD protein (that migrates in an SDS-polyacrylamide gel as a 110 kD protein) which depends on the presence of elevated levels of calcium inside the cell for its activity. The $cPLA_2$ of U.S. Pat. No. 5,322,776 plays a pivotal role in the production of leukotrienes and prostaglandins initiated by the action of pro-inflammatory cytokines and calcium mobilizing agents. The $cPLA_2$ of U.S. Pat. No. 5,322,776 is activated by phosphorylation on serine residues and increasing levels of intracellular calcium, resulting in translocation of the enzyme from the cytosol to the membrane where arachidonic acid is selectively hydrolyzed from membrane phospholipids.

In addition to the $cPLA_2$ of U.S. Pat. No. 5,322,776, some cells contain calcium independent phospholipase $A_2$ (and/or phospholipase B) enzymes. For example, such enzymes have been identified in rat, rabbit, canine and human heart tissue (Gross, TCM, 1991, 2:115; Zupan, et at., Journal of Medicinal Chemistry, 1993, 36: 95; Hazen, et al., Journal of Clinical Investigators, 1993, 91:2513; Lehman, et al., Journal of Biological Chemistry, 1993, 268:20713; Zupan, et al., Journal of Biological Chemistry, 1992, 267:8707; Hazen, et al., Journal of Biological Chemistry, 1991, 266:14526; Loeb, et al., Journal of Biological Chemistry, 1986, 261:10467; Wolf, et al., Journal of Biological Chemistry, 1985, 260:7295; Hazen, et al., Methods in Enzymology, 1991, 197:400; Hazen, et al., Journal of Biological Chemistry, 1990, 265:10622; Hazen, et al., Journal of Biological Chemistry, 1993, 268:9892; Ford, et al., Journal of Clinical Investigators, 1991, 88:331; Hazen, et al., Journal of Biological Chemistry, 1991, 266:5629; Hazen, et al., Circulation Research, 1992, 70:486; Hazen, et al., Journal of Biological Chemistry, 1991, 266:7227; Zupan, et al., FEBS, 1991, 284:27), as well as rat and human pancreatic islet cells (Ramanadham, et al., Biochemistry, 1993, 32:337; Gross, et al., Biochemistry, 1993, 32:327), in the macrophage-like cell line, P388D1 (Ulevitch, et al., Journal of Biological Chemistry, 1988, 263:3079; Ackermann, et al., Journal of Biological Chemistry, 1994, 269:9227; Ross, et al., Arch. Biochem. Biophys., 1985, 238:247; Ackermann, et al., FASEB Journal, 1993, 7(7):1237), in various rat tissue cytosols (Nijssen, et al., Biochim. Biophys. Acta, 1986, 876:611; Pierik, et al., Biochim. Biophys. Acta, 1988, 962:345; Aarsman, et al., Journal of Biological Chemistry, 1989, 264:10008), bovine brain (Ueda, et al., Biochem. Biophys. Res. Comm., 1993, 195:1272; Hirashima, et al., Journal of Neurochemistry, 1992, 59:708), in yeast (Saccharomyces cerevisiae) mitochondria (Yost, et al., Biochemistry International, 1991, 2–4:199), hamster heart cytosol (Cao, et al., Journal of Biological Chemistry, 1987, 262:16027), rabbit lung microsomes (Angle, et al., Biochim. Biophys. Acta, 1988, 962:234) and guinea pig intestinal brush-border membrane (Gassama-Diagne, et al., Journal of Biological Chemistry, 1989, 264:9470).

It is believed that the calcium independent phospholipase $A_2$/B enzymes may perform important functions in release of arachidonic acid in specific tissues which are characterized by unique membrane phospholipids, by generating lysophospholipid species which are deleterious to membrane integrity or by remodeling of unsaturated species of membrane phospholipids through deacylation/reacylation mechanisms. The activity of such a phospholipase may well be regulated by mechanisms that are different from that of the $cPLA_2$ of U.S. Pat. No. 5,322,776. In addition the activity may be more predominant in certain inflamed tissues over others. Although the enzymatic activity is not dependent on calcium this does not preclude a requirement for calcium in vivo, where the activity may be regulated by the interaction of other protein(s) whose function is dependent upon a calcium flux.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See, e.g., H. Dugas and C. Penney, BIOORGANIC CHEMISTRY, (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl
Asp, cyclohexyl
Glu, cyclohexyl
Ser, Benzyl
Thr, Benzyl
Tyr, 4-bromo carbobenzoxy Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees centigrade or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., Methods in Enzymology, 68:109 (1979). See also, J. Sambrook, et al., supra.

The basic steps in the recombinant production of desired proteins are:
 a) construction of a synthetic or semi-synthetic DNA encoding the protein of interest;
 b) integrating said DNA into an expression vector in a manner suitable for the expression of the protein of interest, either alone or as a fusion protein;
 c) transforming an appropriate eukaryotic or prokaryotic host cell with said expression vector,
 d) culturing said transformed or transfected host cell in a manner to express the protein of interest; and
 e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
|---|---|
| DH5α | F− (φ80dlacZΔM15), Δ(lacZYA-argF)U169 supE44, λ−, hsdR17($r_K$−, $m_K$+), recA1, endA1, gyrA96, thi-1, relA1 |
| HB101 | supE44, hsdS20($r_B$−$m_B$−), recA13, ara-14, proA2 lacY1, galK2, rpsL20, xyl-5, mtl-1, mcrB, mrr |
| JM109 | recA1, e14−(mcrA), supE44, endA1, hsdR17($r_K$−, $m_K$+), gyrA96, relA1, thi-1, ΔE(lac-proAB), F′[traD36, proAB+ lacIq,lacZΔEM15] |
| RR1 | supE44, hsdS20($r_B$−$m_B$−), ara-14 proA$_2$, lacY1, galK2, rpsL20, xyl-5, mtl-5 |
| χ1776 | F−, ton, A53, dapD8, minA1, supE42 (glnV42), Δ(gal-uvrB)40, minB2, rfb-2, gyrA$_2$5, thyA142, oms-2, metC65, oms-1, Δ(bioH-asd)29, cycB2, cycA1, hsdR2, λ− |
| 294 | endA, thi−, hsr−, hsm$_k$+ (U.S. Pat. No. 4,366,246) |
| LE392 | F−, hsdR5l4 (r−m−), supE44, supF58, lacY1, or Δlac(I-Y)6, galK2, glaT22, metB1, trpR55, λ− |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra. A preferred strain of *E. coli* employed in the cloning and expression of the genes of this invention is RV308, which is available from the ATCC under accession number ATCC 31608, and is described in U.S. Pat. No. 4,551,433, issued Nov. 5, 1985.

In addition to the strains of *E. coli* discussed supra, bacilli such as Bacillus subtilis, other enterobacteriaceae such as *Salmonella typhimurium* or *Serratia marcescans*, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., *Nature* (London), 275:615(1978); and Goeddel et al., *Nature* (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in PROTEIN PURIFICATION: FROM MOLECULAR MECHANISMS TO LARGE SCALE PROCESSES, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the human phospholipase A$_2$-encoding nucleic acids of the present invention. Exemplary host cells suitable for use in the present invention are listed in Table I

TABLE I

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| 293 | Human Embryonal Kidney | ATCC CRL 1573 |

TABLE I-continued

| Host Cell | Origin | Source |
|---|---|---|
| Sf9 | Fall armyworm ovary *Spodoptera frugiperda* | ATCC CRL-1711 |
| HS-Sultan | Human Plasma Cell Plasmocytoma | ATCC CCL 1484 |
| BHK-21 | Baby Hamster Kidney | ATCC CCL 10 |

An especially preferred mammalian cell line employed in this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

The most preferred cell line employed in the expression of the protein of the present invention is the Sf9 cell line.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and poly-adenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein.

Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA)*, 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. No. 5,242,688, issued Sep. 7, 1993, and U.S. Pat. No. 4,992,373, issued Feb. 12, 1991, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See. e.g., J. Sambrook, et al., supra, at 3:16.30–3:16.66.

The most preferred expression vector employed in the present invention is derived from the vector pVL1393 (STRATAGENE). This vector system employs the aforementioned Sf9 cell line.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See. eg., L. Stinchcomb, et al., *Nature* (London), 282:39 (1979); J. Kingsman et al., *Gene,* 7:141 (1979); S. Tschemper et al., *Gene,* 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC 1 promoter on plasmid YEpsec--hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which1 are functional equivalents of the protein of SEQ ID NO:2 are shown in Table II, infra.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:3 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human phospholipase $A_2$ molecule may be produced using synthetic methodology. This synthesis of nucleic acids is well known in the art. See, e.g., E. L. Brown, R. Belagaje, M. J. Ryan, and H. G. Khorana, *Methods in Enzymology* 68:109–151 (1979). The DNA segments corresponding to the gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See. e.g., M. J. Gait, ed., OLIGONUCLEOTIDE SYNTHESIS, A PRACTICAL APPROACH, (1984).

The synthetic human phospholipase $A_2$ gene may be designed to possess restriction endonuclease cleavage sites at either end of the transcript to facilitate isolation from and integration into expression and amplification plasmids. The restriction sites are chosen so as to properly orient the coding sequence of the target enzyme with control sequences to achieve proper in-frame reading and expression of the phospholipase $A_2$ molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid compounds described supra the present invention also encompasses the ribonucleic acid compounds having the following sequence

| | | | | | | |
|---|---|---|---|---|---|---|
| CCGUGACCCC | AGAUGGUUAC | GCGGAUGCCG | UGAGAGGGGA | UCGCUUCAUG | AUGCCAGCUG | 60 |
| AGCGCCGCCU | GCCCCUGAGC | UUCGUGCUGG | AUGUGCUGGA | GGGCCGGGCC | CAGCACCCUG | 120 |
| GAGUCCUCUA | UGUGCAGAAG | CAGUGCUCCA | ACCUGCCCAG | CGAGCUGCCC | CAGCUGCUGC | 180 |
| CUGAUCUGGA | AUCCCAUGUG | CCCUGGGCCU | CCGAAGCCCU | GGGAAAGAUG | CCCGAUGCUG | 240 |
| UGAACUUCUG | GCUGGGGGAG | GCGGCUGCAG | UGACUUCUUU | GCACAAGGAC | CACUAUGAGA | 300 |
| ACCUCUACUG | CGUGGUCUCA | GGAGAGAAGC | AUUUCCUGUU | CCAUCCGCCC | AGCGACCGGC | 360 |
| CCUUCAUCCC | CUAUGAGCUG | UACACGCCGG | CAACCUACCA | GCUAACUGAA | GAGGGCACCU | 420 |
| UUAAGGUGGU | GGAUGAAGAG | GCCAUGGAGA | AGGCAGAGGU | GUCCAGGACC | UGCCUGCUCA | 480 |
| CGGUUCGUGU | CCUGCAGGCC | CAUCGCCUAC | CCUCUAAGGA | CCUAGUGACC | CCCUCUGACU | 540 |
| GCUACGUGAC | UCUCUGGCUG | CCCACGGCCU | GCAGCCACAG | GCUCCAGACA | CGCACGGUCA | 600 |
| AGAACAGCAG | UAGCUCUGUC | UGGAACCAGA | GCUUUCACUU | CAGGAUCCAC | AGGCAGCUCA | 660 |
| AGAAUGUCAU | GGAACUGAAA | GUCUUUGACC | AGGACCUGGU | GACCGGAGAU | GACCCUGUGU | 720 |
| UGUCAGUACU | GUUUGAUGCG | GGGACUCUGC | GGGCUGGGGA | GUUCCGGCGC | GAGAGCUUCU | 780 |
| CACUGAGCCC | UCAGGGUGAG | GGGCGCCUGG | AAGUUGAAUU | UCGCCUGCAG | AGUCUGGCUG | 840 |
| ACCGUGGCGA | GUGGCUCGUC | AGCAAUGGCG | UUCUGGUGGC | CCGGGAGCUC | UCCUGCUUGC | 900 |
| ACGUUCAACU | GGAGGAGACA | GGAGACCAGA | AGUCCUCAGA | GCACAGAGUU | CAGCUUGUGG | 960 |
| UUCCUGGGUC | CUGUGAGGGU | CCGCAGGAGG | CCUCUGUGGG | CACUGGCACC | UUCCGCUUCC | 1020 |
| ACUGCCCAGC | CUGCUGGGAG | CAGGAGCUGA | GUAUUCGCCU | GCAGGAUGCC | CCCGAGGAGC | 1080 |
| AACUAAAGGC | GCCACUGAGU | GCCCUGCCCU | CUGGUCAAGU | GGUGAGGCUU | GUCUUCCCCA | 1140 |
| CGUCCCAGGA | GCCCCUGAUG | AGAGUGGAGC | UGAAAAAAGA | AGCAGGACUG | AGGGAGCUGG | 1200 |
| CCGUGCGACU | GGGCUUCGGG | CCCUGUGCAG | AGGAGCAGGC | CUUCCUGAGC | AGGAGGAAGC | 1260 |
| AGGUGGUGGC | CGCGGCCUUG | AGGCAGGCCC | UGCAGCUGGA | UGGAGACCUG | CAGGAGGAUG | 1320 |
| AGAUCCCAGU | GGUAGCUAUU | AUGGCCACUG | GUGGUGGGAU | CCGGGCAAUG | ACUUCCCUGU | 1380 |
| AUGGGCAGCU | GGCUGGCCUG | AAGGAGCUGG | GCCUCUUGGA | UUGCGUCUCC | UACAUCACCG | 1440 |
| GGGCCUCGGG | CUCCACCUGG | GCCUUGGCCA | ACCUUUAUGA | GGACCCAGAG | UGGUCUCAGA | 1500 |
| AGGACCUGGC | AGGGCCCACU | GAGUUGCUGA | AGACCCAGGU | GACCAAGAAC | AAGCUGGGUG | 1560 |
| UGCUGGCCCC | CAGCCAGCUG | CAGCGGUACC | GGCAGGAGCU | GGCCGAGCGU | GCCCGCUUGG | 1620 |
| GCUACCCAAG | CUGCUUCACC | AACCUGUGGG | CCCUCAUCAA | CGAGGCGCUG | CUGCAUGAUG | 1680 |
| AGCCCCAUGA | UCACAAGCUC | UCAGAUCAAC | GGGAGGCCCU | GAGUCAUGGC | CAGAACCCUC | 1740 |
| UGCCCAUCUA | CUGUGCCCUC | AACACCAAAG | GCAGAGCCU | GACCACUUUU | GAAUUUGGGG | 1800 |
| AGUGGUGCGA | GUUCUCUCCC | UACGAGGUCG | GCUUCCCCAA | GUACGGGCC | UUCAUCCCCU | 1860 |
| CUGAGCUCUU | UGGCUCCGAG | UUCUUUAUGG | GGCAGCUGAU | GAAGAGGCUU | CCUGAGUCCC | 1920 |
| GCAUCUGCUU | CUUAGAAGGU | AUCUGGAGCA | ACCUGUAUGC | AGCCAACCUC | CAGGACAGCU | 1980 |
| UAUACUGGGC | CUCAGAGCCC | AGCCAGUUCU | GGGACCGCUG | GGUCAGGAAC | CAGGCCAACC | 2040 |

```
-continued

UGGACAAGGA GCAGGUCCCC CUUCUGAAGA UAGAAGAACC ACCCUCAACA GCCGGCAGAA  2100

UAGCUGAGUU UUUCACCGAU CUUCUGACGU GGCGUCCACU GGCCCAGGCC ACACAUAAUU  2160

UCCUGCGUGG CCUCCAUUUC CACAAAGACU ACUUUCAGCA UCCUCACUUC UCCACAUGGA  2220

AAGCUACCAC UCUGGAUGGG CUCCCCAACC AGCUGACACC CUCGGAGCCC CACCUGUGCC  2280

UGCUGGAUGU UGGCUACCUC AUCAAUACCA GCUGCCUGCC CCUCCUGCAG CCCACUCGGG  2340

ACGUGGACCU CAUCCUGUCA UUGGACUACA ACCUCCACGG AGCCUUCCAG CAGUUGCAGC  2400

UCCUGGGCCG GUUCUGCCAG GAGCAGGGGA UCCCGUUCCC ACCCAUCUCG CCCAGCCCCG  2460

AAGAGCAGCU CCAGCCUCGG GAGUGCCACA CCUUCUCCGA CCCCACCUGC CCCGGAGCCC  2520

CUGCGGUGCU GCACUUUCCU CUGGUCAGCG ACUCCUUCCG GGAGUACUCG GCCCCUGGGG  2580

UCCGGCGGAC ACCCGAGGAG GCGGCAGCUG GGGAGGUGAA CCUGUCUUCA UCGGACUCUC  2640

CCUACCACUA CACGAAGGUG ACCUACAGCC AGGAGGACGU GGACAAGCUG CUGCACCUGA  2700

CACAUUACAA UGUCUGCAAC AACCAGGAGC AGCUGCUGGA GGCUCUGCGC CAGGCAGUGC  2760

AGCGGAGGCG GCAGCGCAGG CCCCACUGAU GGCCGGGGCC CCUGCCACCC CUAACUCUCA  2820

UUCAUUCCCU GGCUGCUGAG UUGCAGGUGG GAACUGUCAU CACGCAGUGC UUCAGAGCCU  2880

CGGGCUCAGG UGGCACUGUC CCAGGGUCCA GGCUGAGGGC UGGGAGCUCC CUUGCGCCUC  2940

AGCAGUUUGC AGUGGGGUAA GGAGGCCAAG CCCAUUUGUG UAAUCACCCA AAACCCCCCG  3000

GCCUGUGCCU GUUUUCCCUU CUGCGCUACC UUGAGUAGUU GGAGCACUUG AUACAUCACA  3060

GACUCAUACA AAAAAAAAAA AAAAA                                       3085
``` hereinafter referred to as SEQ ID NO:4, or the complementary ribonucleic acid, or a fragment of either SEQ ID NO:4 or the complement thereof. The ribonucleic acids of the present invention may be prepared using the polynucleotide synthetic methods discussed supra or they may be prepared enzymatically using any one of various RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1, SEQ ID NO:2 or SEQ ID NO:4.

The present invention also provides probes and primers useful for molecular biology techniques. A compound which is SEQ ID NO: 1, SEQ ID NO:2, SEQ ID NO:4 or a complementary sequence of SEQ ID NO:1, SEQ ID NO:2 or SEQ ID NO:4, or a fragment thereof, and which is at least 18 base pairs in length, and which will selectively hybridize to genomic DNA or messenger RNA encoding a phospholipase $A_2$, is provided. Preferably, the 18 or more base pair compound is DNA.

The term "selectively hybridize" as used herein may refer to either of two situations. In the first such embodiment of this invention, the nucleic acid compounds described supra hybridize DNA or RNA encoding a human phospholipase $A_2$ under more stringent hybridization conditions than these same nucleic acid compounds would hybridize to an analogous phospholipase $A_2$ of another species, e.g. murine or primate. In the second such embodiment of this invention, these probes hybridize to DNA or RNA encoding a phospholipase $A_2$ of the present invention under more stringent hybridization conditions than other related compounds, including nucleic acid sequences encoding other human phospholipase $A_2$ enzymes.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:2.

Yet another embodiment of the invention is a method of using a $cPLA_2$-encoding gene to transform a cell. There is a wide variety of transformation techniques applicable to both prokaryotic and eukaryotic cells which will not be discussed, because such methods are old in the art.

A further embodiment of the invention consists of a method of using a host cell to express $cPLA_2$. In this embodiment, a host cell, either prokaryotic or eukaryotic, that has been transformed is cultured in an appropriate medium until a substantial cell mass has been obtained. Fermentation of transformed prokaryotes and mass cell culture of transformed eukaryotic cells is well known in the art and will not be discussed for that reason.

The second step of this embodiment is the isolation of $cPLA_2$ from the cultured cells. Two methods for purifying $cPLA_2$ from a non-transformed mammalian cell line are described in U.S. Pat. No. 5,328,842, the entire contents of which are herein incorporated by reference. The following summarizes those methods.

Once grown and harvested, the cultured cells are lysed by nitrogen cavitation in the presence of protease inhibitors. A soluble fraction is prepared from the lysate by ultracentrifugation. The resulting solution of cytosolic proteins contains $cPLA_2$ and is subjected to a series of purification procedures.

The soluble fraction of the cell lysate is run through a series of column chromatography procedures. Anion exchange chromatography is followed by hydrophobic interaction, molecular sizing and finally another hydrophobic interaction technique where the conditions are such that the $cPLA_2$ binds the resin weakly. Each column is run individually, and the eluate is collected in fractions while monitoring for absorbance at 280 nm. Fractions are assayed for phospholipase $A_2$ activity, and those fractions with the desired activity are then run over the next column until a homogeneous solution of $cPLA_2$ is obtained.

Immunoaffinity purification using anti-$cPLA_2$ antibodies is an alternative to the series of chromatographic procedures already mentioned. Making antiserum or monoclonal antibodies directed against a purified protein is well known in the art, and skilled artisans readily will be able to prepare anti-$cPLA_2$ antibodies. Preparing an immunoaffinity matrix using such antibodies and isolating $cPLA_2$ using the immunoaffinity matrix is also well within the skill of the art. See, AFFINITY CHROMATOGRAPHY PRINCIPLES & METHODS, Pharmacia Fine Chemicals, 1983.

The invention also encompasses a method of using a $cPLA_2$-encoding gene to screen compounds. By using purified, recombinantly, or even naturally produced $cPLA_2$, it is possible to test whether a particular compound is able to inhibit or block $cPLA_2$ enzyme activity. By adding the test compound over a wide range of concentrations to the substrate solution described in Example 1 below, it is trivial to determine whether a given compound is able to inhibit or block the enzyme's activity.

The following examples will help describe how the invention is practiced and will illustrate the characteristics of the claimed $cPLA_2$-encoding genes, vectors, host cells, and methods of the invention.

EXAMPLE 1
$cPLA_2$ Enzymatic Activity Assay

The substrate, sonicated liposomes containing 1-palmitoyl-2-[$^{14}C$]arachidonoyl-sn-glycero-3-phosphocholine ([$^{14}C$]PC, 55 mCi/mmol from NEN Research Products) and sn-1,2-dioleoylglycerol (DG, Avanti Polar Lipids, Birmingham, Ala.) at a molar ratio of 2:1, is prepared as follows. [$^{14}C$]PC (20 nmol, 1×10$^6$ dpm, 50 $\mu$Ci/ml in toluene/ethanol) and DG (10 nmol, 100 $\mu$g/ml in chloroform) are dried under nitrogen. The lipids are dispersed in 1 ml of 150 mM NaCl, 50 mM HEPES, pH 7.5 (assay buffer) by sonication at 4° C., with a Microson probe-sonicator (Heat Systems Ultrasonics) for 4×15 seconds, with 45 second intervals. Bovine serum albumin (essentially fatty acid free, from a 100 mg/ml stock in water, Sigma) is added to a final concentration of 4 mg/ml. Samples to be assayed for $cPLA_2$ activity are incubated with 50 $\mu$l liposomes (0.5 nmol [$^{14}C$]PC, 50,000 dpm containing 0.25 nmol of DG) in a total volume of 0.2 ml of assay buffer containing 1 mM $CaCl_2$ and 1 mM 2-mercaptoethanol. Incubations are carried out at 37° C. for 15 minutes and terminated by adding 2 ml of Dole's reagent (2-propanol/heptane/0.5M sulfuric acid, 40:10:1 containing 10 $\mu$g/ml of stearic acid). After mixing, 1.2 ml of heptane and 1 ml of water are added. The mixtures are briefly vortexed and the upper phase transferred to tubes containing 2 ml of heptane and 150 mg of BIO-SIL™ (Bio-Rad Laboratories), activated at 130° C. before use. The tubes are thoroughly vortexed and centrifuged (1000×g for 5 minutes). The supernatants are decanted into scintillation vials. After addition of 10 ml of a liquid scintillation cocktail (Ready Protein+, Beckman) radioactivity is counted using a Beckman liquid scintillation counter Model LS 7000. High radioactive counts correlate with enzymatic activity.

EXAMPLE 2
Prokaryotic Expression of $cPLA_2$

*E. coli* strains are prepared that contain a vector of the present invention. Preferably the strains carried closed circular plasmids that contain $cPLA_2$-encoding cDNA, a tetracycline resistance-conferring gene, the temperature sensitive cI857 repressor that regulates the lambda pL promoter and other regulatory elements necessary for transcription and translation in *E. coli*. The host cell is grown overnight in Tryptone broth supplemented with 10 $\mu$g/ml tetracycline (TY) at 28° C., then diluted 1:10 with the TY broth and agitated for 60 minutes at 28° C. After the initial growth phase, the cells are induced by raising the culture temperature to 42° C. for six hours. The induced cells are lysed by treatment with a 1 mg/ml (final concentration in water) lysozyme solution and sonicated six times for 15 seconds, at 45 second intervals. A transformed and a non-transformed cell lysate are prepared and assayed for protein content. The samples are then assayed for $cPLA_2$ activity according to Example 1.

EXAMPLE 3
Eukaryotic Expression of $cPLA_2$

Transient expression of $cPLA_2$ is achieved in the human embryonal kidney cell line 293. The line is a permanent part of the American Type Culture Collection (ATCC) and is available under accession number CRL 1573.

A) Plasmid Isolation

One half liter of DS broth (12 gm tryptone, 24 gm yeast extract, 4 ml glycerol, 100 ml of 0.17M $KH_2PO_4$+0.72M $K_2HPO_4$ per liter) containing 100 $\mu$g/ml ampicillin is inoculated with *E. coli* K12 DH5 alpha cells containing a suitable vector of the present invention and incubated in an air shaker at 37° C. overnight.

The culture is then removed and centrifuged in a Sorvalt GSA rotor (Dupont Co., Instrument Products, Newtown, Conn. 06470) at 7500 rpm for 10 minutes at 4° C. The resulting supernatant is discarded, and the cell pellet is resuspended in 14 mls of a solution of 25% sucrose and 50 mM Tris/HCl (Sigma), pH 8.0; the mixture is then transferred to an oakridge tube. Two milliliters of a 10 mg/ml lysozyme solution and 0.75 ml of 0.5M ethylene diamine tetraacetic acid (EDTA) pH 8.4, are added to the solution, which is then incubated on ice for 15 minutes. 1.5 mls of Triton lytic mix (3% Triton X-100 (Sigma), 0.19M EDTA, 0.15M Tris/HCl pH 8.0) is added to the solution, which is then incubated for 15 minutes. The solution is centrifuged in a Sorvall SS34 rotor (Dupont Co., Instrument products, Newtown, Conn. 06470) at 20,000 rpm for 45 minutes at 4° C. The resulting supernatant containing plasmid DNA is removed and mixed with a solution of 20.55 g CsCl, 0.28 ml of 1M Tris/HCl pH 8.0, and 1.35 ml of a 10 mg/ml ethidium bromide (EtBr) solution. The final volume of the mixture is brought to 27 ml with water. The mixture is centrifuged in two Quick-seal tubes (Beckman Cat. #342413) in a Ti 75 rotor (Beckman Instruments, Inc.) at 45,000 rpm for 4 days at 20° C. Plasmid bands are collected separately into two new Quick-seal tubes. One hundred fifty microliters of EtBr (10 mg/ml) is added into each tube and then the tubes are topped off with a CsCl/$H_2O$ (double distilled, deionized water) solution (density=1.56 g/ml) and centrifuged in a Ti 75 rotor at 45,000 rpm for 24 hours at 20° C.

The plasmid band is collected and an equal volume of water is added to dilute the CsCl. Ethidium bromide is extracted 5 times with between 2 and 3 volumes of 1-butanol. Absolute ethanol (2.5 volumes) is added to the extracted solution containing plasmid, which is incubated at room temperature for 5–10 minutes and then centrifuged in a Soyall SS34 rotor at 10,000 rpm for 10 minutes. The DNA pellet is dried and then dissolved in 200 μl of TE solution (1 mM EDTA, 10 mM Tris/HCl pH 8.0).

B) Transfection of Eukaryotic Cell Line 293

One day prior to transfection, 293 cells are seeded in two, 100 $cm^2$ culture dishes (Falcon #1005) at a density of $1\times10^6$ cells per dish. The cells are seeded and grown in DMEM (Dulbecco's Modified Eagle Medium; GIBCO, Grand Island, N.Y.) supplemented with 10% fetal bovine serum (Hyclone; Ogden, Utah) and 50 mg/ml of gentamycin (GIBCO) in a 5% carbon dioxide, humidified 37° C. incubator. Approximately 20 μg of purified plasmid DNA is added to a calcium phosphate transfection buffer (see Wigler, et al., *Proceedings of the National Academy of Sciences* (USA), 76, (1979) in the absence of any carrier DNA. The transfection is allowed to proceed for four hours at 37° C., after which the transfection buffer is replaced with DMEM, supplemented as described above, and the cells are allowed to grow for three days.

C) Cell Lysis

The transfected cultures are washed once with wash buffer (140 mM NaCl, 5 mM KCl, 2 mM EDTA, 25 mM HEPES, pH 7.4) and are removed from the culture dishes by adding 10 ml of wash buffer followed by scraping. The cells (approximately $1\times10^7$) are placed in a conical tube and centrifuged. One milliliter of wash buffer plus 1 mM phenylmethane sulfonyl fluoride, 100 μM leupeptin and 100 μM pepstatin A is added to the pellet and the cells are lysed using a probe sonicator (Model W-385, Heat Systems Ultrasonics) with a stepped microtip at an output setting of 1. Sonication is repeated six times for 15 seconds at 45 second intervals.

The transfected 293 lysates are then assayed for $cPLA_2$ activity according to Example 1.

EXAMPLE 4

Stable Eukaryotic Expression of $cPLA_2$

Stable expression of $cPLA_2$ is achieved in the human embryohal kidney cell line 293 and in the AV12 hamster cell line. The AV12 cell line is a permanent part of the ATCC and is available under accession number CRL9595, and the 293 cell line is a permanent part of the ATCC and is available under accession number CRL1573. Plasmids containing the $cPLA_2$-encoding gene are prepared according to Example 3 A).

Both mammalian cell lines are transfected with an appropriate plasmid according to Example 3B) except that the plasmid DNA is first linearized by digestion with an appropriate restriction enzyme and precipitated with ethanol. After transfection, both cell lines are individually seeded into culture plates and grown for three days in DMEM after which the medium is replaced with selective medium (e.g., DMEM supplemented as described above plus 200 ug/ml hygromycin) to kill any cells which did not take up the linearized plasmid DNA.

After 5 days, most of the originally seeded cells will have spontaneously detached from the culture plates and are removed by the weekly changes of medium (twice weekly for AV12 cells); however, colonies will grow from both cell lines. These colonies are transferred to 24-well trays (Costar Inc.) using plastic pipet tips.

The transfected lines are grown and assayed as described in Examples 1 and 3. The negative controls are the non-transformed cell lines handled in the same fashion. The results clearly show that stable cell lines expressing $bPLA_2$ are obtained by transformation with vectors of the invention.

EXAMPLE 5

Western Blot Analysis

Immunological and electrophoretic equivalence between naturally-occurring $cPLA_2$, described in U.S. Pat. No. 5,328, 842, and recombinant $bPLA_2$ produced using one of the DNA sequences of the present invention, is established by western blot analysis.

Monoclonal antibodies specific for $cPLA_2$ are described in U.S. Pat. No. 5,328,842. Similarly, monoclonal antibodies are raised against the protein of the present invention. One of those antibodies is used as the primary antibody to probe the blot for $PLA_2$ in the present example. The primary antibody, at a concentration of 0.5 mg/ml, is diluted 1:570 in TBST plus 0.02% sodium azide. The protein-containing blot is incubated overnight at 4° C. in the primary antibody solution and then washed as before.

The blot is then washed as before, followed by incubation at 4° C. overnight in a 1:500 dilution (TBST) of goat anti-rabbit IgG conjugated to horseradish peroxidase. The blot is washed and developed for 60 minutes at room temperature in a solution of 42 ml of 0.1M phosphate buffer, pH 6; 8 ml of 4-chloronapthol (3 mg/ml in methanol) containing 300 μls of 3% hydrogen peroxide.

DNA Sequencing

Sequence determinations are performed with dideoxy chain termination with an automated flourescent dye DNA sequencer (Applied Biosystems) or manually using [α-$^{35}$S] dATP followed by autoradiography. For manual sequencing either a T7 primer or a M13F (forward) primer is used.

Generation of a PCR Probe for Screening of Library

A PCR product is generated with the $PLA_2$ clone as a template with primers appropriately chosen under the following conditions: 1 minute at 94° C., 1 minute at 55° C. and 2 minutes at 72° C. for 25 cycles. The product is labeled with [α-$^{32}$P]dCTP using a random priming method. The probe is purified on a SEPHADEX G-50™ column to remove non-incorporated nucleotides.

Screening of a Human Genomic Library

A human genomic DNA library made from lymphocytes in a commercially available lambda vector, lambda DASH™, is plated out with *E. coli* LE 392 as bacterial host strain. Hybridizations are carried out for 16 hours with high stringency at 65° C. in 25% formamide, 6×SSC, 10% Dextran sulfate, 5×Denhardt's solution and 0.1% SDS. Plaques are lifted with nylon membranes. Filters are washed twice at room temperature in 2×SSC, 0.5% SDS and twice for 30 minutes at 65° C. in 0.2×SSC, 0.5% SDS. The filters are exposed on film. Screenings are carried out in three consecutive steps and single plaques are picked in the tertiary screening. A number of strongly hybridizing plaques are selected and a high titer stock is made for amplification of the phages.

Phage Clone Characterization

Phages are grown in *E. coli* LE 392 in liquid culture. Phage particles are collected and DNA is extracted and digested with various restriction enzymes and run on agarose gel. The gel is denatured and blotted onto a nylon membrane. The membrane is hybridized as described above with the rat probe and exposed on film. Hybridizing fragments are identified and cloned into the commonly used plasmid vector Bluescript KS+. Plasmid DNA is prepared using commercially available kits. A restriction map is constructed for overlapping hybridizing clones.

Cloning into Expression Vector

If no suitable restriction sites are available in the PLA$_2$ clone for cloning into the expression vector, two oligonucleotides may be used as primers to generate a fragment containing the entire coding region, or a substantial segment thereof, employing PCR technology.

The PCR is run with VENT DNA POLYMERASE™ (a commercially available DNA polymerase cloned from the archaebacterium *Thermococcus litoralis*, New England Biolabs, Beverly, Mass.) and the PLA$_2$ clone as a template under the following conditions: 1 minute at 94° C., 1 minute at 50° C. and 2 minutes at 72° C. for 25 cycles. An aliquot of the PCR reaction is run on an agarose gel and displays the expected product of 1.25 kb. The remainder of the reaction is phenol extracted, cut with the appropriate restriction enzymes and run on a preparative agarose gel and collected onto a DEAE membrane. The DNA is eluted from the membrane and purified by phenol extraction. The fragment is then ligated into the expression vector.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The desired plasmid may be isolated from *E. coli* containing these plasmids using standard procedures such as cesium chloride DNA isolation or isolation in a QIAGEN™ column.

Any plasmid comprising the gene of the present invention is readily modified to construct expression vectors that produce phospholipase A$_2$ in a variety of organisms, including, for example, *E. coli*, Sf9 (as host for baculovirus), Spodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, CURRENT PROTOCOLS IN MOLECULAR BIOLOGY, 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oligonucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and *E. coli* cells which have been transfected and/or transformed with a vector which comprises a nucleic acid of the present invention.

The present invention also provides a method for constructing a recombinant host cell capable of expressing SEQ ID NO:3, said method comprising transforming a host cell with a recombinant DNA vector that comprises an isolated DNA sequence which encodes SEQ ID NO:3. The preferred host cell is AV12. The preferred vector for expression is one which comprises SEQ ID NO:2. Another preferred host cell for this method is *E. coli*. An especially preferred expression vector in *E. coli* is one which comprises SEQ ID NO:2. Transformed host cells may be cultured under conditions well known to skilled artisans such that SEQ ID NO:2 is expressed, thereby producing the phospholipase A$_2$ in the recombinant host cell.

The ability of an agent to inhibit the protein of the present invention is essential in the development of a multitude of indications. In developing agents which act as inhibitors of phospholipase A$_2$, it would be desirable, therefore, to determine those agents which interact with the protein of the present invention. Generally, such an assay includes a method for determining whether a substance is a functional ligand of phospholipase A$_2$, said method comprising contacting a functional compound of the phospholipase A$_2$ with said substance, monitoring enzymatic activity by physically detectable means, and identifying those substances which effect a chosen response.

The instant invention provides such a screening system useful for discovering agents which inhibit the phospholipase $A_2$, said screening system comprising the steps of:

a) isolating a phospholipase $A_2$;

b) exposing said phospholipase $A_2$ to a potential inhibitor of the phospholipase $A_2$;

c) quantifying the activity of the phospholipase $A_2$ relative to a control in which no potential inhibitor is introduced.

This allows one to rapidly screen for inhibitors of phospholipase $A_2$. Utilization of the screening system described above provides a sensitive and rapid means to determine compounds which inhibit phospholipase $A_2$. This screening system may also be adapted to automated procedures such as a PANDEX® (Baxter-Dade Diagnostics) system allowing for efficient high-volume screening of potential therapeutic agents.

Pharmaceutical compositions containing anti-inflammatory agents (i.e., inhibitors) identified by the screening method of the present invention may be employed to treat, for example, a number of inflammatory conditions such as rheumatoid arthritis, psoriasis, asthma, inflammatory bowel disease and other diseases mediated by increased levels of prostaglandins, leukotriene, or platelet activating factor. Pharmaceutical compositions of the invention comprise a therapeutically effective amount of a calcium independent $cPLA_2$ inhibitor compound first identified according to the present invention in a mixture with an optional pharmaceutically acceptable carrier. The term "pharmaceutically acceptable" means a non-toxic material that does not interfere with the effectiveness of the biological activity of the active ingredient(s). The term "therapeutically effective amount" means the total amount of each active component of the method or composition that is sufficient to show a meaningful patient benefit, i.e., healing or amelioration of chronic conditions or increase in rate of healing or amelioration. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the inhibitor of this invention is contemplated to be in the range of about 0.1 µg to about 100 mg per kg body weight per application. It is contemplated that the duration of each application of the inhibitor will be in the range of 12 to 24 hours of continuous administration. The characteristics of the carrier or other material will depend on the route of administration.

The amount of inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not increased further.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See. e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', $Fab_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See, e.g., C. Milstein, HANDBOOK OF EXPERIMENTAL IMMUNOLOGY, (Blackwell Scientific Pub., 1986); J. Goding, MONOCLONAL ANTIBODIES: PRINCIPLES AND PRACTICE, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See. e.g. R. E. Bird, et al., *Science* 242:423–426 (1988); PCT Publication No. WO 88/01649, which was published Mar. 10, 1988; U.S. Pat. No. 5,260,203, issued Nov. 9, 1993, the entire contents of which are herein incorporated by reference. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of phospholipase $A_2$.

In addition to being functional as direct therapeutic and diagnostic aids, the availability of a family of antibodies which are specific for phospholipase $A_2$ enables the development of numerous assay systems for detecting agents which bind to this receptor. One such assay system comprises radiolabeling phospholipase $A_2$-specific antibodies with a radionuclide such as $^{125}I$ and measuring displacement of the radiolabeled phospholipase $A_2$-specific antibody from solid phase phospholipase $A_2$ in the presence of a potential inhibitor.

Numerous other assay systems are also readily adaptable to detect agents which bind phospholipase $A_2$. Examples of these aforementioned assay systems are discussed in *Methods in Enzymology*, (J. Langone. and H. Vunakis, eds. 1981), Vol. 73, Part B, the contents of which are herein incorporated by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for phospholipase $A_2$, this invention also provides antibodies which are specific for the hypervariable regions of the phospholipase $A_2$ antibodies. Some such anti-idiotypic antibodies would resemble the original epitope, the phospholipase $A_2$, and, therefore, would be useful in evaluating the effectiveness of compounds which are potential inhibitors of the phospholipase $A_2$. See. e.g., Cleveland, et al., *Nature* (London), 305:56 (1983); Wasserman, et al., *Proceedings of the National Academy of Sciences (USA)*, 79:4810 (1982).

In another embodiment, this invention encompasses pharmaceutical formulations for parenteral administration which contain, as the active ingredient, the anti-phospholipase $A_2$ antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

Immunocytochemistry

Immunocytochemistry has demonstrated increased numbers of reactive astrocytes containing cytosolic phospholipase $A_2$ in the astrocytes of brains from patients suffering from Alzheimer's disease. See, U.S. Pat. No. 5,478,857, issued Dec. 26, 1995, the entire contents of which are herein incorporated by reference. Immunochemistry is performed on paraffin sections from human occipital cortex of persons afflicted with Alzheimer's disease as well as normal persons. In each case the tissue is fixed only briefly (60–90 minutes) and then transferred to Tris-buffered saline for several days prior to embedding. The monoclonal antibody M12 is raised against purified $cPLA_2$ from U937 cells using standard techniques. Ascites are produced in BALB/c mice and antibodies are affinity-purified using Protein A Fast Flow™ resin. The antibody M12 recognizes the native form of $cPLA_2$ and is also a neutralizing antibody. A rabbit antiserum to glial fibrillary acidic protein (GFAP; Biogenex Labs, San Ramon, Calif.) is used to label astrocytes.

Immunostaining of tissue sections (10 $\mu$M) utilizes conventional immunoperoxidase techniques and employed the avidin-biotin peroxidase system (ABC, Vector Laboratories, Burlingame, Calif.). For $cPLA_2$ localization, 0.1 mg/ml M12 antibody is used. Anti-GFAP is obtained as prediluted antisera. Dual localization is carried out by sequential immunostaining. An alkaline phosphatase-streptavidin system (Biogenex Labs) using Fast Red™ as chromagen is used to localize the rabbit antibody (GFAP) and nickel chloride-enhanced DAB (Vector Laboratories) is used to detect the peroxidase-labeled mouse anti-$cPLA_2$.

These immunochemistry studies demonstrate localization of $cPLA_2$ in protoplasmic astrocytes in the gray matter and provide further evidence for the importance of this cell type in inflammatory processes in the brain. Comparison of normal adult brains with those brains from persons afflicted with Alzheimer's disease evinces the role of cytosolic phospholipase $A_2$ in the inflammatory component of this disease.

Such experiments are also performed using antibodies raised against the $PLA_2$ of the present invention as described supra.

We claim:
1. An isolated amino acid having the sequence depicted in SEQ ID NO:3.

\* \* \* \* \*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 8517 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1611..2063

(ix) FEATURE:
        (A) NAME/KEY: exon
        (B) LOCATION: 5315..6045

(ix) FEATURE:
        (A) NAME/KEY: exon
        (B) LOCATION: 6143..6758

(ix) FEATURE:
        (A) NAME/KEY: exon
        (B) LOCATION: 7075..7317

(ix) FEATURE:
        (A) NAME/KEY: exon
        (B) LOCATION: 7473..8499

(xi) SEQUENCE DESCRIPTION: SEQ ID NO:1:

```
CTAGAATTCA GCGGCCGCTT TTTTTTTTTT TTTTTTTTTT TTTTTTTGAG ATAAAGTCTT      60

GCTCTGTCAC CCAGGCTGGA GTGCAGTGGC ACGATGATAG CTCATTGCAG CCTCTACCTC     120

TTGGACTCAA GTGATCCTCT GGCTTCAGCC TCTAGCGTAG CTAGGAGTAT AGGTGCATGC     180

CACCATGTCC AGTTAATTTT TAATTTTTTT GTAGAGATGG GGTCTCCCTA CGTTGCCAAG     240

GCTGGTCTTG ACCTCCCGGC CTCAGCAATC CTCCTGCCTC TGCCTCCCAA AGTGCTGGGA     300

TTACAGACAT GAGCCACCAC GTCTAGCCCT AAAATATATA GCATGTCAGA TGGTGATGAA     360

TGCTAACGAG AAAAAATACG GAAAGGGATA TAAAGATTTG CGGCAGGGGG ACAGATTATA     420

AATTTAGAAA GTATAGTCAG AGAAGGAAGT CTTATCAATG TGATATTTGA GTGAGGACCC     480

AAAGGAGGTA GCTGGAATGT GGATGCCAGT GGAGGAGAGG AGACGGTGGG TTTGAGAGAC     540

ATAGGAGACA GAATCAACAG GACTCAGAGC CAATCAGTAG GATGACGGGA GTGAAGGAGA     600

AAGCTGAGTC AAAAAGATTT TGATTAGAGG TGACACAGGG CCACTGTAGA CCCCTGCGCA     660

GGCGGCACAC CACGCAGCCT GCCGAAGTGT ACGTGGTGGC CCTGGGTGTC TGGAGATGGT     720

GATGCTGTTC AGCAGGACCC AAACCATAGC CGAGCCCTTC CTTTTCCTCC ATTGGTGTCA     780

TCTGGTAGTT TGTCTTCCCG GGTAAGAAGG TTGTAAATTT CTTAAGATGA TGATTGTGTC     840

ATCCCTGATA GCCCCAGATT AGCCAAGCCA AGTGCTGAGC ACATTCCTGG TGCTCAGTAA     900

ATGTCACTGT TAAAGGGGGC TTCCCAGAGC CACACAACAC CCAGAATAGC CCGTGGCCAT     960

GGGGCCTCAG CCTTACTCAT TCTGGAGCTC CCAGTGCCAC TTCCATGGTG GCCTTTCCTG    1020

GTAGATGCTA GGAGGCTGGC CTCTCCAGGG TGGGAAGGCA TAGGGTCCAC TGTGCAGACA    1080

CAGCCCCACA GGGGATTTGG CTTATGGGCT GGGTAGCAGC CTCTGGCCCT GTGGATGGTC    1140

AGGGCCCATG CTGGTGTGTG TGCGTGATGC TTTCTGCTTT CATTTTTCCA TCCTCATCTT    1200
```

-continued

```
TCTATTACTG GTTGTCCAGG GTCCTTTGGT CACCAACGAG CATTTCCCAG TGACACAGCG   1260

CGGCCTTTCC AGGGAGGGCA TCTCTTGGGC AGGGACTGGG TGCTGCAGAC ATCAGCCCTT   1320

CCATCCCCTG TCTTCTTCTT TCTCTCAGAG CTCTGCGTGC CTCTTGCTGT GCCCTACCTG   1380

GACAAACCCC CAACTCCGCT CCACTTCTAC CGGGACTGGG TCTGCCCCAA CAGGCCGTGC   1440

ATTATCCGCA ACGCTCTGCA GCACTGGCCG GCCCTCCAGA AGTGGTCCCT CCCCTATTTC   1500

AGGTGGGAGC TGCCCTGGGG TCAGGTGTGA GCAGTGATTA CTGGCATCTG GCATGGGCT    1560

GAGTGTCCAT TCCTCTAGAG CCACAGTGGG CTCCACAGAG GTGAGTGTGG CCGTGACCCC   1620

AGATGGTTAC GCGGATGCCG TGAGAGGGGA TCGCTTCATG ATGCCAGCTG AGCGCCGCCT   1680

GCCCCTGAGC TTCGTGCTGG ATGTGCTGGA GGGCCGGGCC CAGCACCCTG GAGTCCTCTA   1740

TGTGCAGAAG CAGTGCTCCA ACCTGCCCAG CGAGCTGCCC CAGCTGCTGC CTGATCTGGA   1800

ATCCCATGTG CCCTGGGCCT CCGAAGCCCT GGGAAAGATG CCCGATGCTG TGAACTTCTG   1860

GCTGGGGGAG GCGGCTGCAG TGACTTCTTT GCACAAGGAC CACTATGAGA ACCTCTACTG   1920

CGTGGTCTCA GGAGAGAAGC ATTTCCTGTT CCATCCGCCC AGCGACCGGC CCTTCATCCC   1980

CTATGAGCTG TACACGCCGG CAACCTACCA GCTAACTGAA GAGGGCACCT TAAGGTGGT    2040

GGATGAAGAG GCCATGGAGA AGGTGCCCTG GATCCCACTG GACCCCTTGG CGCCAGACCT   2100

AGCACGGTAC CCTAGTTACA GTCAGGCCCA GGCCCTTCGC TGCACGGTGC GGGCCGGTGA   2160

GATGCTCTAT CTGCCGGCTC TGTGGTTCCA CCACGTCCAG CAGTCCCAGG GCTGCATCGC   2220

AGTGAATTTC TGGTATGACA TGGAATACGA CCTCAAGTAT AGTTACTTCC AGCTGCTCGA   2280

CTCCCTCACC AAGGTTTCAG GCCTTGACTG ATGGAGCACT GGTGAACACG ACCAAGCACG   2340

CCTCGGGGGA CGGAGCCAGC CCCTCCCTGG CCAGGTCAAT TCTCGAGAGA GCCTGGAGTG   2400

TGCATGCTGG CTGCTGGCCC CGGGTCCAGC ATGGCTTGAG ATCAGCTTTG GAGGATCTTG   2460

GAATGTGGTC ATAAGGACTC AAGGTGCCAG GCAGGTCTGG GTGAGGGTTC TCAGGAAGTT   2520

GCCACACAGG TGAGCAGAGT GGGGATCAGG TGCAGCGGCA CCTCTCCCCA GCGCTGTGAT   2580

GTTGGGCGAG TCACTGCGTC TCGGGCATTG GTGTCCTGTC AGTAAAGAGA TAATAATGGC   2640

TGTACCTCGC GGGGCTGTTG TGGGCTTGGA GATGATGTCT ATGAGGACCA GCATGGAGCT   2700

GGCACACAGG ACATGTTGAA TAAAAGGTAG CTGTGAGTCG TATGTCCTTT TTTTTTTTT    2760

TTTAAGATGG GGTCTCGCTC TGTCACCCAG GCTGGAGTGC AGTGGTGTGA TGTCAGCTCA   2820

CTGCAAGCTC CGCCTCCCAG GTTCACACTA TTCTGCCTCA GCCTCCCAAG TAGCTGGGAC   2880

TACAGGTGCG TGCCACCATG CCCGGCTAAT TTTTTTGTAT TTTTAGTAGA GACGGGGTTT   2940

CACCGTGTTA GCCAGTATGG TCTTGATCTC CTGACCTCGT GATCCACCTG CCTCGGCCTC   3000

CCAAAAGTGC TGGGATTACA GGTGTGAGCT GCTGCGCCTG GCTTATGAGT CGTATGTTCT   3060

GATCCTCCCT CTTGAAGTTG CCTTCTGTGG TCTAAGGAGG GCCTGAAGGT TCAGGTAAAA   3120

ACTTCAGGGT GACCTTCACT GGGGGTGAGG GCTGGATCCC AGCCTGGGCC CAAAGAGCCG   3180

TCAGCTGCCC AAGTCCCGCT GTCCATGAGA GTCACCGCAG CCCCTCCCTG GACAAGCAA    3240

GCAGACCTGA GTCTTGTAGC TCTCTGGTCC GGACCTCTTT GGCCCAGGAC CTTGAGAGCT   3300

ATTCCTAGCT CTCCTATGGT TACTGTCCTC CCCCAGTTCA GGGGCAGCAG GTGGGACCTG   3360

GTGCCCTGGG GATAACCCCT GTTTCTCCCA TAACAGGCAC AGGCAGGAAG GGACGGAAGC   3420

CCCCGCCTCT CCTGGGGCTG TCCCTCTGAG GAAAGAGTTG GTCTCACACA GCTGACCCCC   3480

CCACAAACCA TGCCCTGGAG GCAGAAGAAC CCCCTGCCCC TGAGTGCCAA CCCACAGGCC   3540
```

```
-continued

TCATCCCTGG CCACTCAGCA CCTAGCTTTG AAGGGCTGTT TTATGTGACA GCCACTCCCC    3600

TGCCTGTCGT GAGGGGGCCC GGGTGTTCAT CTCAGATTGA TGGATCCCTG CCATCAAGAC    3660

TGGGCATTCC TGTCCAACAG GTGCCAGAGT TGCGAAAGGC CTGTGACAGG GAACTCCACT    3720

CTTCCCTTGG CTGCTGTTCT GGGACTCACC CCTGCTTTCC TTCTGCTCAG CCCCTGGCAG    3780

CAAGCTCTCC AGGCTGGGAT TGCAGGGCTG GGTGGGGCAG GCCCAGCTGG TAAAGGCTGG    3840

CGAGTGCCAC AGAGGTATCA GGAGCTCTAG TATAGGCTTA GGGTGCCTCA TTTCCTGGAC    3900

AGGTGGCTGG TTCAGGAGTG GGTGTGGAGC TTAGGTGGAG CAGAGGCGGC GGGTAGGAGG    3960

GACTTGGGAC CAATTGGGAC ATCACATCCC TGGCTCTGGG TTAGAAAGCT GACAGTCCTT    4020

GATCCTGTGG CCACTGCCCC ATCATTCCTG CTCCTGAGGA CTCAGTCTCA TGGCTGTGGT    4080

AAGGCCTGGC AGGGCCCTGG GTCCCTACTG GGACCCCTGG TCCTCCTACC TGGGGCCTAG    4140

TTAATATGTT TCCTTATGGG AGCTGTGGTC TTCTCCAGGG GTAGGGAGGG GAGTTTATTG    4200

ACCACAAGAC CAGGGTAGCG GGCAGAAGCC AGGGGAGGAG GAGGCTTGGG GATGAGGGAT    4260

CCGTCCTGAG TGTTTTCTGT CCTGGGAACG GGCTCCTGGC AGAGCTCCCT GGCACCACAG    4320

ATTTGGGCCC TGGAGACTCA GAGGCTCCCA GCTGCCGCCC TGAGGCCCTG GAAGCAAGTG    4380

GCTCCTCCAT GCTCCTCTGA CTCAGTTGCC TGGAGTGTGA GGGCCCTGGG CTGACCCTGG    4440

TGGATGAGGC CCTCCAGCAC TGCCCTGGAC CTGGTTGCTC CCTGGACTTG ACCTGTTAGG    4500

GTCCTTGTGG AGGCAGGTGG GAGGCCGAAA GGAAACAGTT GGCACAGGCT TCCCTGGTCC    4560

CGGTGCGCCT GCCAGGCTGC ATTCCCAGAA CCAGGGGCAT GGGTTTGGAG GGAGCTACCG    4620

GGGGACCATC TTCAGCCTGA CCTGGCAGGA CCTGGAGGAC ATGACAGCCT GTGAGGGGTC    4680

TGAGCTAGGA GCCGCCTCCC CTGCCCAGGA GAGAGCCCAT TTCCAGGATG CTCTTCTGAC    4740

CAGGGTGGAG GGAGGGTACG AGAGCAGCTC AGCCTGGGGC CCAAGGCCCT GATGTGCTAC    4800

TTCCCCTCCC TCGATAGCTT ATGTCCCCTG CCACCCAAGA CCAGCCGGAA AGCTGCTTGG    4860

CTGGGGTGTG GGCTGGGGAT GTGGGGTGGA GAGCCTAAAG GATACTAGCC CGAGAAGGTG    4920

GAAGCAGGTC TGTGTGAGGC ATAAATCTGG AGCCAGCCTG CCCGGGCTCC AACCCCAATT    4980

GTGGACCTCA GGCAAGTGAC TGCTTCTCTG TGCCTCAGTT TCCTTGTGGA GTGGGCCATC    5040

GTAAATAGTA TCTGTGCATA AGGTGGTTGT GCGATAAATG AGTTAATGTA TGCAAAGCCC    5100

TTGGCCCAGA GCCGGCGCAG AGCATTGTGT AAGTGCTGGC AGGCGTCATG ATGGAGATAT    5160

GATGTCTCCT CTTGTTGATT CAGGATTCTG ATGAGATGGA GGATGGGCCT GGGGTTCAGG    5220

ATTAGGTCTT GAGGCACTGC TCCAGCCTCC TTTGTGGCCC CTGTCACCCT TGGCTTCATC    5280

GGCCCGTAGC AGGTCTCCCC TCTCCCACCT CTGCAGGCAG AGGTGTCCAG GACCTGCCTG    5340

CTCACGGTTC GTGTCCTGCA GGCCCATCGC CTACCCTCTA AGGACCTAGT GACCCCCTCT    5400

GACTGCTACG TGACTCTCTG GCTGCCCACG GCCTGCAGCC ACAGGCTCCA GACACGCACG    5460

GTCAAGAACA GCAGTAGCCC TGTCTGGAAC CAGAGCTTTC ACTTCAGGAT CCACAGGCAG    5520

CTCAAGAATG TCATGGAACT GAAAGTCTTT GACCAGGACC TGGTGACCGG AGATGACCCT    5580

GTGTTGTCAG TACTGTTTGA TGCGGGGACT CTGCGGGCTG GGGAGTTCCG GCGCGAGAGC    5640

TTCTCACTGA GCCCTCAGGG TGAGGGCGC CTGGAAGTTG AATTTCGCCT GCAGAGTCTG    5700

GCTGACCGTG GCGAGTGGCT CGTCAGCAAT GGCGTTCTGG TGGCCCGGGA GCTCTCCTGC    5760

TTGCACGTTC AACTGGAGGA GACAGAGACC AGAAGTCCTC AGAGCACAGA GTCAGCTTGT    5820

GTTCCTGGTC CTGTGAGGTC CGCAGGAGGC CTCTGTGGGC ACTGGCACCT TCCGCTTCCA    5880

CTGCCCAGCC TGCTGGGAGC AGGAGCTGAG TATTCGCCTG CAGGATGCCC CCGAGGAGCA    5940
```

-continued

```
ACTAAAGGCG CCACTGAGTG CCCTGCCCTC TGGTCAAGTG GTGAGGCTTG TCTTCCCCAC      6000

GTCCCAGGAG CCCCTGATGA GAGTGGAGCT GAAAAAAGAA GCAGGGCTGG AGTGCAATGG      6060

CGTGATCTTG GCTCACTGCA ACCTCCGCCT CTGGGGTTCA AGCGATTCTC CTGCCTCAGC      6120

CTCCCGAGTA GCTGGGATTA CAGACTGAGG GAGCTGGCCG TGCGACTGGG CTTCGGGCCC      6180

TGTGCAGAGG AGCAGGCCTT CCTGAGCAGG AGGAAGCAGG TGGTGGCCGC GGCCTTGAGG      6240

CAGGCCCTGC AGCTGGATGG AGACCTGCAG GAGGATGAGA TACCCAGTGG TAGCTATTAT      6300

GGCCACTGGT GGTGGGATCC GGGCAATGAC TTCCCTGTAT GGGCAGCTGG CTGGCCTGAA      6360

GGAGCTGGGC CTCTTGGATT GCGTCTCCTA CATCACCGGG GCCTCGGGCT CCACCTGGGC      6420

CTTGGCCAAC CTTTATGAGG ACCCAGAGTG GTCTCAGAAG GACCTGGCAG GGCCCACTGA      6480

GTTGCTGAAG ACCCAGGTGA CCAAGAACAA GCTGGGTGTG CTGGCCCCCA GCCAGCTGCA      6540

GCGGTACCGG CAGGAGCTGG CCGAGCGTGC CCGCTTGGGC TACCCAAGCT GCTTCACCAA      6600

CCTGTGGGCC CTCATCAACG AGGCGCTGCT GCATGATGAG CCCCATGATC ACAAGCTCTC      6660

AGATCAACGG GAGGCCCTGA GTCATGGCCA GAACCCTCTG CCCATCTACT GTGCCCTCAA      6720

CACCAAAGGG CAGAGCCTGA CCACTTTTGA ATTTGGGGGT GAGTGGCCCA AGAGCTGAGA      6780

CCTGTGCCCT TGCAGTTGGT GGAATAAGGG GAGAACGAGG ACTGTGTGCA GATTGCAGAT      6840

GTCACACCCA CCTCTCCTGA GCCAGGTCCC GTGCTTTCTG GAGACCGGCA CCCTACCAGG      6900

GTCCCTCAGC CCTTTGGGAA GGAGGCAGGG GCCTTAGGTC CTATGCACGA AGCCCAGGCC      6960

ACAAGGCCTG GCCTCCTGG TCCTCAGCTG CCCTAAAGCA AAACCCTGGG TCGGGGTGGG      7020

GGTGTGGGTG CCTAAGGGCT CTGCACCATG AGGCTGAGGC GTGGACTCCT CACAGAGTGG      7080

TGCGAGTTCT CTCCCTACGA GGTCGGCTTC CCCAAGTACG GGGCCTTCAT CCCCTCTGAG      7140

CTCTTTGGCT CCGAGTTCTT TATGGGGCAG CTGATGAAGA GGCTTCCTGA GTCCCGCATC      7200

TGCTTCTTAG AAGGTATCTG GAGCAACCTG TATGCAGCCA ACCTCCAGGA CAGCTTATAC      7260

TGGGCCTCAG AGCCCAGCCA GTTCTGGGAC CGCTGGGTCA GGAACCAGGC CAACCTGGGT      7320

AAGTGCTCCG GGCCCTTCAT AAGGGTGCCA AGGGGCAGCC AGCTGGGGCT GCACCAGGGG      7380

GCGGGGGTT CACACCTCTT CCCCCTCCAG GGTCACCACC AAGGTGGGGA TAAAGGTGCA      7440

GGAGTCCCCA TTTCCCCCAC CTTGCCTGTG TAGACAAGGA GCAGGTCCCC CTTCTGAAGA      7500

TAGAAGAACC ACCCTCAACA GCCGGCAGGA TAGCTGAGTT TTTCACCGAT CTTCTGACGT      7560

GGCGTCCACT GGCCCAGGCC ACACATAATT TCCTGCGTGG CCTCCATTTC CACAAAGACT      7620

ACTTTCAGCA TCCTCACTTC TCCACATGGA AAGCTACCAC TCTGGATGGG CTCCCCAACC      7680

AGCTGACACC CTCGGAGCCC CACCTGTGCC TGCTGGATGT TGGCTACCTC ATCAATACCA      7740

GCTGCCTGCC CCTCCTGCAG CCCACTCGGG ACGTGGACCT CATCCTGTCA TTGGACTACA      7800

ACCTCCACGG AGCCTTCCAG CAGTTGCAGC TCCTGGGCCG GTTCTGCCAG GAGCAGGGGA      7860

TCCCGTTCCC ACCCATCTCG CCCAGCCCCG AAGAGCAGCT CCAGCCTCGG GAGTGCCACA      7920

CCTTCTCCGA CCCCACCTGC CCCGGAGCCC CTGCGGTGCT GCACTTTCCT CTGGTCAGCG      7980

ACTCCTTCCG GGAGTACTCG GCCCCTGGGG TCCGGCGGAC ACCCGAGGAG GCGGCAGCTG      8040

GGGAGGTGAA CCTGTCTTCA TCGGACTCTC CCTACCACTA CACGAAGGTG ACCTACAGCC      8100

AGGAGGACGT GGACAAGCTG CTGCACCTGA CACATTACAA TGTCTGCAAC AACCAGGAGC      8160

AGCTGCTGGA GGCTCTGCGC CAGGCAGTGC AGCGGAGGCG GCAGCGCAGG CCCCACTGAT      8220

GGCCGGGGCC CCTGCCACCC CTAACTCTCA TTCATTCCCT GGCTGCTGAG TTGCAGGTGG      8280
```

-continued

```
GAACTGTCAT CACGCAGTGC TTCAGAGCCT CGGGCTCAGG TGGCACGGTC CCAGGGTCCA      8340

GGCTGAGGGC TGGGAGCTCC CTTGCGCCTC AGCAGTTTGC AGTGGGGTAA GGAGGCCAAG      8400

CCCATTTGTG TAATCACCCA AAACCCCCCG GCCTGTGCCT GTTTTCCCTT CTGCGCTACC      8460

TTGAGTAGTT GGAGCACTTG ATACATCACA GACTCATACA AAAAAAAAAA AAAAAA         8517
```

(2) INFORMATION FOR SEQ ID NO:2:

(i) SEQUENCE CHARACTERISTICS:
        (A) LENGTH: 3085 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 48..2786

(xi) SEQUENCE DESCRIPTION: SEQ ID NO:2:

```
CCGTGACCCC AGATGGTTAC GCGGATGCCG TGAGAGGGGA TCGCTTC ATG ATG CCA              56
                                                 Met Met Pro
                                                   1

GCT GAG CGC CGC CTG CCC CTG AGC TTC GTG CTG GAT GTG CTG GAG GGC            104
Ala Glu Arg Arg Leu Pro Leu Ser Phe Val Leu Asp Val Leu Glu Gly
      5                  10                  15

CGG GCC CAG CAC CCT GGA GTC CTC TAT GTG CAG AAG CAG TGC TCC AAC            152
Arg Ala Gln His Pro Gly Val Leu Tyr Val Gln Lys Gln Cys Ser Asn
 20                  25                  30                  35

CTG CCC AGC GAG CTG CCC CAG CTG CTG CCT GAT CTG GAA TCC CAT GTG            200
Leu Pro Ser Glu Leu Pro Gln Leu Leu Pro Asp Leu Glu Ser His Val
                 40                  45                  50

CCC TGG GCC TCC GAA GCC CTG GGA AAG ATG CCC GAT GCT GTG AAC TTC            248
Pro Trp Ala Ser Glu Ala Leu Gly Lys Met Pro Asp Ala Val Asn Phe
             55                  60                  65

TGG CTG GGG GAG GCG GCT GCA GTG ACT TCT TTG CAC AAG GAC CAC TAT            296
Trp Leu Gly Glu Ala Ala Ala Val Thr Ser Leu His Lys Asp His Tyr
         70                  75                  80

GAG AAC CTC TAC TGC GTG GTC TCA GGA GAG AAG CAT TTC CTG TTC CAT            344
Glu Asn Leu Tyr Cys Val Val Ser Gly Glu Lys His Phe Leu Phe His
 85                  90                  95

CCG CCC AGC GAC CGG CCC TTC ATC CCC TAT GAG CTG TAC ACG CCG GCA            392
Pro Pro Ser Asp Arg Pro Phe Ile Pro Tyr Glu Leu Tyr Thr Pro Ala
100                 105                 110                 115

ACC TAC CAG CTA ACT GAA GAG GGC ACC TTT AAG GTG GTG GAT GAA GAG            440
Thr Tyr Gln Leu Thr Glu Glu Gly Thr Phe Lys Val Val Asp Glu Glu
                120                 125                 130

GCC ATG GAG AAG GCA GAG GTG TCC AGG ACC TGC CTG CTC ACG GTT CGT            488
Ala Met Glu Lys Ala Glu Val Ser Arg Thr Cys Leu Leu Thr Val Arg
            135                 140                 145

GTC CTG CAG GCC CAT CGC CTA CCC TCT AAG GAC CTA GTG ACC CCC TCT            536
Val Leu Gln Ala His Arg Leu Pro Ser Lys Asp Leu Val Thr Pro Ser
        150                 155                 160

GAC TGC TAC GTG ACT CTC TGG CTG CCC ACG GCC TGC AGC CAC AGG CTC            584
Asp Cys Tyr Val Thr Leu Trp Leu Pro Thr Ala Cys Ser His Arg Leu
    165                 170                 175

CAG ACA CGC ACG GTC AAG AAC AGC AGT AGC TCT GTC TGG AAC CAG AGC            632
Gln Thr Arg Thr Val Lys Asn Ser Ser Ser Ser Val Trp Asn Gln Ser
180                 185                 190                 195

TTT CAC TTC AGG ATC CAC AGG CAG CTC AAG AAT GTC ATG GAA CTG AAA            680
Phe His Phe Arg Ile His Arg Gln Leu Lys Asn Val Met Glu Leu Lys
```

```
                 200                 205                 210
GTC TTT GAC CAG GAC CTG GTG ACC GGA GAT GAC CCT GTG TTG TCA GTA      728
Val Phe Asp Gln Asp Leu Val Thr Gly Asp Asp Pro Val Leu Ser Val
            215                 220                 225

CTG TTT GAT GCG GGG ACT CTG CGG GCT GGG GAG TTC CGG CGC GAG AGC      776
Leu Phe Asp Ala Gly Thr Leu Arg Ala Gly Glu Phe Arg Arg Glu Ser
        230                 235                 240

TTC TCA CTG AGC CCT CAG GGT GAG GGG CGC CTG GAA GTT GAA TTT CGC      824
Phe Ser Leu Ser Pro Gln Gly Glu Gly Arg Leu Glu Val Glu Phe Arg
    245                 250                 255

CTG CAG AGT CTG GCT GAC CGT GGC GAG TGG CTC GTC AGC AAT GGC GTT      872
Leu Gln Ser Leu Ala Asp Arg Gly Glu Trp Leu Val Ser Asn Gly Val
260                 265                 270                 275

CTG GTG GCC CGG GAG CTC TCC TGC TTG CAC GTT CAA CTG GAG GAG ACA      920
Leu Val Ala Arg Glu Leu Ser Cys Leu His Val Gln Leu Glu Glu Thr
                280                 285                 290

GGA GAC CAG AAG TCC TCA GAG CAC AGA GTT CAG CTT GTG GTT CCT GGG      968
Gly Asp Gln Lys Ser Ser Glu His Arg Val Gln Leu Val Val Pro Gly
            295                 300                 305

TCC TGT GAG GGT CCG CAG GAG GCC TCT GTG GGC ACT GGC ACC TTC CGC     1016
Ser Cys Glu Gly Pro Gln Glu Ala Ser Val Gly Thr Gly Thr Phe Arg
        310                 315                 320

TTC CAC TGC CCA GCC TGC TGG GAG CAG GAG CTG AGT ATT CGC CTG CAG     1064
Phe His Cys Pro Ala Cys Trp Glu Gln Glu Leu Ser Ile Arg Leu Gln
    325                 330                 335

GAT GCC CCC GAG GAG CAA CTA AAG GCG CCA CTG AGT GCC CTG CCC TCT     1112
Asp Ala Pro Glu Glu Gln Leu Lys Ala Pro Leu Ser Ala Leu Pro Ser
340                 345                 350                 355

GGT CAA GTG GTG AGG CTT GTC TTC CCC ACG TCC CAG GAG CCC CTG ATG     1160
Gly Gln Val Val Arg Leu Val Phe Pro Thr Ser Gln Glu Pro Leu Met
                360                 365                 370

AGA GTG GAG CTG AAA AAA GAA GCA GGA CTG AGG GAG CTG GCC GTG CGA     1208
Arg Val Glu Leu Lys Lys Glu Ala Gly Leu Arg Glu Leu Ala Val Arg
            375                 380                 385

CTG GGC TTC GGG CCC TGT GCA GAG GAG CAG GCC TTC CTG AGC AGG AGG     1256
Leu Gly Phe Gly Pro Cys Ala Glu Glu Gln Ala Phe Leu Ser Arg Arg
        390                 395                 400

AAG CAG GTG GTG GCC GCG GCC TTG AGG CAG GCC CTG CAG CTG GAT GGA     1304
Lys Gln Val Val Ala Ala Ala Leu Arg Gln Ala Leu Gln Leu Asp Gly
    405                 410                 415

GAC CTG CAG GAG GAT GAG ATC CCA GTG GTA GCT ATT ATG GCC ACT GGT     1352
Asp Leu Gln Glu Asp Glu Ile Pro Val Val Ala Ile Met Ala Thr Gly
420                 425                 430                 435

GGT GGG ATC CGG GCA ATG ACT TCC CTG TAT GGG CAG CTG GCT GGC CTG     1400
Gly Gly Ile Arg Ala Met Thr Ser Leu Tyr Gly Gln Leu Ala Gly Leu
                440                 445                 450

AAG GAG CTG GGC CTC TTG GAT TGC GTC TCC TAC ATC ACC GGG GCC TCG     1448
Lys Glu Leu Gly Leu Leu Asp Cys Val Ser Tyr Ile Thr Gly Ala Ser
            455                 460                 465

GGC TCC ACC TGG GCC TTG GCC AAC CTT TAT GAG GAC CCA GAG TGG TCT     1496
Gly Ser Thr Trp Ala Leu Ala Asn Leu Tyr Glu Asp Pro Glu Trp Ser
        470                 475                 480

CAG AAG GAC CTG GCA GGG CCC ACT GAG TTG CTG AAG ACC CAG GTG ACC     1544
Gln Lys Asp Leu Ala Gly Pro Thr Glu Leu Leu Lys Thr Gln Val Thr
    485                 490                 495

AAG AAC AAG CTG GGT GTG CTG GCC CCC AGC CAG CTG CAG CGG TAC CGG     1592
Lys Asn Lys Leu Gly Val Leu Ala Pro Ser Gln Leu Gln Arg Tyr Arg
500                 505                 510                 515

CAG GAG CTG GCC GAG CGT GCC CGC TTG GGC TAC CCA AGC TGC TTC ACC     1640
```

-continued

```
              Gln Glu Leu Ala Glu Arg Ala Arg Leu Gly Tyr Pro Ser Cys Phe Thr
                              520                 525                 530

AAC CTG TGG GCC CTC ATC AAC GAG GCG CTG CTG CAT GAT GAG CCC CAT           1688
Asn Leu Trp Ala Leu Ile Asn Glu Ala Leu Leu His Asp Glu Pro His
            535                 540                 545

GAT CAC AAG CTC TCA GAT CAA CGG GAG GCC CTG AGT CAT GGC CAG AAC           1736
Asp His Lys Leu Ser Asp Gln Arg Glu Ala Leu Ser His Gly Gln Asn
        550                 555                 560

CCT CTG CCC ATC TAC TGT GCC CTC AAC ACC AAA GGG CAG AGC CTG ACC           1784
Pro Leu Pro Ile Tyr Cys Ala Leu Asn Thr Lys Gly Gln Ser Leu Thr
    565                 570                 575

ACT TTT GAA TTT GGG GAG TGG TGC GAG TTC TCT CCC TAC GAG GTC GGC           1832
Thr Phe Glu Phe Gly Glu Trp Cys Glu Phe Ser Pro Tyr Glu Val Gly
580                 585                 590                 595

TTC CCC AAG TAC GGG GCC TTC ATC CCC TCT GAG CTC TTT GGC TCC GAG           1880
Phe Pro Lys Tyr Gly Ala Phe Ile Pro Ser Glu Leu Phe Gly Ser Glu
                600                 605                 610

TTC TTT ATG GGG CAG CTG ATG AAG AGG CTT CCT GAG TCC CGC ATC TGC           1928
Phe Phe Met Gly Gln Leu Met Lys Arg Leu Pro Glu Ser Arg Ile Cys
            615                 620                 625

TTC TTA GAA GGT ATC TGG AGC AAC CTG TAT GCA GCC AAC CTC CAG GAC           1976
Phe Leu Glu Gly Ile Trp Ser Asn Leu Tyr Ala Ala Asn Leu Gln Asp
        630                 635                 640

AGC TTA TAC TGG GCC TCA GAG CCC AGC CAG TTC TGG GAC CGC TGG GTC           2024
Ser Leu Tyr Trp Ala Ser Glu Pro Ser Gln Phe Trp Asp Arg Trp Val
    645                 650                 655

AGG AAC CAG GCC AAC CTG GAC AAG GAG CAG GTC CCC CTT CTG AAG ATA           2072
Arg Asn Gln Ala Asn Leu Asp Lys Glu Gln Val Pro Leu Leu Lys Ile
660                 665                 670                 675

GAA GAA CCA CCC TCA ACA GCC GGC AGA ATA GCT GAG TTT TTC ACC GAT           2120
Glu Glu Pro Pro Ser Thr Ala Gly Arg Ile Ala Glu Phe Phe Thr Asp
                680                 685                 690

CTT CTG ACG TGG CGT CCA CTG GCC CAG GCC ACA CAT AAT TTC CTG CGT           2168
Leu Leu Thr Trp Arg Pro Leu Ala Gln Ala Thr His Asn Phe Leu Arg
            695                 700                 705

GGC CTC CAT TTC CAC AAA GAC TAC TTT CAG CAT CCT CAC TTC TCC ACA           2216
Gly Leu His Phe His Lys Asp Tyr Phe Gln His Pro His Phe Ser Thr
        710                 715                 720

TGG AAA GCT ACC ACT CTG GAT GGG CTC CCC AAC CAG CTG ACA CCC TCG           2264
Trp Lys Ala Thr Thr Leu Asp Gly Leu Pro Asn Gln Leu Thr Pro Ser
    725                 730                 735

GAG CCC CAC CTG TGC CTG CTG GAT GTT GGC TAC CTC ATC AAT ACC AGC           2312
Glu Pro His Leu Cys Leu Leu Asp Val Gly Tyr Leu Ile Asn Thr Ser
740                 745                 750                 755

TGC CTG CCC CTC CTG CAG CCC ACT CGG GAC GTG GAC CTC ATC CTG TCA           2360
Cys Leu Pro Leu Leu Gln Pro Thr Arg Asp Val Asp Leu Ile Leu Ser
                760                 765                 770

TTG GAC TAC AAC CTC CAC GGA GCC TTC CAG CAG TTG CAG CTC CTG GGC           2408
Leu Asp Tyr Asn Leu His Gly Ala Phe Gln Gln Leu Gln Leu Leu Gly
            775                 780                 785

CGG TTC TGC CAG GAG CAG GGG ATC CCG TTC CCA CCC ATC TCG CCC AGC           2456
Arg Phe Cys Gln Glu Gln Gly Ile Pro Phe Pro Pro Ile Ser Pro Ser
        790                 795                 800

CCC GAA GAG CAG CTC CAG CCT CGG GAG TGC CAC ACC TTC TCC GAC CCC           2504
Pro Glu Glu Gln Leu Gln Pro Arg Glu Cys His Thr Phe Ser Asp Pro
    805                 810                 815

ACC TGC CCC GGA GCC CCT GCG GTG CTG CAC TTT CCT CTG GTC AGC GAC           2552
Thr Cys Pro Gly Ala Pro Ala Val Leu His Phe Pro Leu Val Ser Asp
820                 825                 830                 835
```

-continued

```
TCC TTC CGG GAG TAC TCG GCC CCT GGG GTC CGG CGG ACA CCC GAG GAG      2600
Ser Phe Arg Glu Tyr Ser Ala Pro Gly Val Arg Arg Thr Pro Glu Glu
            840                 845                 850

GCG GCA GCT GGG GAG GTG AAC CTG TCT TCA TCG GAC TCT CCC TAC CAC      2648
Ala Ala Ala Gly Glu Val Asn Leu Ser Ser Ser Asp Ser Pro Tyr His
        855                 860                 865

TAC ACG AAG GTG ACC TAC AGC CAG GAG GAC GTG GAC AAG CTG CTG CAC      2696
Tyr Thr Lys Val Thr Tyr Ser Gln Glu Asp Val Asp Lys Leu Leu His
        870                 875                 880

CTG ACA CAT TAC AAT GTC TGC AAC AAC CAG GAG CAG CTG CTG GAG GCT      2744
Leu Thr His Tyr Asn Val Cys Asn Asn Gln Glu Gln Leu Leu Glu Ala
        885                 890                 895

CTG CGC CAG GCA GTG CAG CGG AGG CGG CAG CGC AGG CCC CAC              2786
Leu Arg Gln Ala Val Gln Arg Arg Arg Gln Arg Arg Pro His
900                 905                 910

TGATGGCCGG GGCCCCTGCC ACCCCTAACT CTCATTCATT CCCTGGCTGC TGAGTTGCAG     2846

GTGGGAACTG TCATCACGCA GTGCTTCAGA GCCTCGGGCT CAGGTGGCAC TGTCCCAGGG     2906

TCCAGGCTGA GGGCTGGGAG CTCCCTTGCG CCTCAGCAGT TTGCAGTGGG GTAAGGAGGC     2966

CAAGCCCATT TGTGTAATCA CCCAAAACCC CCCGGCCTGT GCCTGTTTTC CCTTCTGCGC     3026

TACCTTGAGT AGTTGGAGCA CTTGATACAT CACAGACTCA TACAAAAAAA AAAAAAAAA     3085

(2) INFORMATION FOR SEQ ID NO:3:

(i) SEQUENCE CHARACTERISTICS:
        (A) LENGTH: 913 amino acids
        (B) TYPE: amino acid
        (D) TOPOLOGY: linear (ii) MOLECULE TYPE: protein (xi) SEQUENCE DESCRIPTION: SEQ ID NO:3:

Met Met Pro Ala Glu Arg Arg Leu Pro Leu Ser Phe Val Leu Asp Val
 1               5                  10                  15

Leu Glu Gly Arg Ala Gln His Pro Gly Val Leu Tyr Val Gln Lys Gln
                20                  25                  30

Cys Ser Asn Leu Pro Ser Glu Leu Pro Gln Leu Leu Pro Asp Leu Glu
            35                  40                  45

Ser His Val Pro Trp Ala Ser Glu Ala Leu Gly Lys Met Pro Asp Ala
        50                  55                  60

Val Asn Phe Trp Leu Gly Glu Ala Ala Val Thr Ser Leu His Lys
 65                 70                  75                  80

Asp His Tyr Glu Asn Leu Tyr Cys Val Val Ser Gly Glu Lys His Phe
                85                  90                  95

Leu Phe His Pro Pro Ser Asp Arg Pro Phe Ile Pro Tyr Glu Leu Tyr
               100                 105                 110

Thr Pro Ala Thr Tyr Gln Leu Thr Glu Glu Gly Thr Phe Lys Val Val
           115                 120                 125

Asp Glu Glu Ala Met Glu Lys Ala Glu Val Ser Arg Thr Cys Leu Leu
       130                 135                 140

Thr Val Arg Val Leu Gln Ala His Arg Leu Pro Ser Lys Asp Leu Val
145                 150                 155                 160

Thr Pro Ser Asp Cys Tyr Val Thr Leu Trp Leu Pro Thr Ala Cys Ser
               165                 170                 175

His Arg Leu Gln Thr Arg Thr Val Lys Asn Ser Ser Ser Val Trp
           180                 185                 190

Asn Gln Ser Phe His Phe Arg Ile His Arg Gln Leu Lys Asn Val Met
```

-continued

```
            195                 200                 205
Glu Leu Lys Val Phe Asp Gln Asp Leu Val Thr Gly Asp Asp Pro Val
    210                 215                 220
Leu Ser Val Leu Phe Asp Ala Gly Thr Leu Arg Ala Gly Glu Phe Arg
225                 230                 235                 240
Arg Glu Ser Phe Ser Leu Ser Pro Gln Gly Glu Gly Arg Leu Glu Val
                245                 250                 255
Glu Phe Arg Leu Gln Ser Leu Ala Asp Arg Gly Glu Trp Leu Val Ser
            260                 265                 270
Asn Gly Val Leu Val Ala Arg Glu Leu Ser Cys Leu His Val Gln Leu
        275                 280                 285
Glu Glu Thr Gly Asp Gln Lys Ser Ser Glu His Arg Val Gln Leu Val
    290                 295                 300
Val Pro Gly Ser Cys Glu Gly Pro Gln Glu Ala Ser Val Gly Thr Gly
305                 310                 315                 320
Thr Phe Arg Phe His Cys Pro Ala Cys Trp Glu Gln Glu Leu Ser Ile
                325                 330                 335
Arg Leu Gln Asp Ala Pro Glu Glu Gln Leu Lys Ala Pro Leu Ser Ala
            340                 345                 350
Leu Pro Ser Gly Gln Val Val Arg Leu Val Phe Pro Thr Ser Gln Glu
        355                 360                 365
Pro Leu Met Arg Val Glu Leu Lys Lys Glu Ala Gly Leu Arg Glu Leu
    370                 375                 380
Ala Val Arg Leu Gly Phe Gly Pro Cys Ala Glu Gln Ala Phe Leu
385                 390                 395                 400
Ser Arg Arg Lys Gln Val Val Ala Ala Leu Arg Gln Ala Leu Gln
                405                 410                 415
Leu Asp Gly Asp Leu Gln Glu Asp Glu Ile Pro Val Val Ala Ile Met
            420                 425                 430
Ala Thr Gly Gly Gly Ile Arg Ala Met Thr Ser Leu Tyr Gly Gln Leu
        435                 440                 445
Ala Gly Leu Lys Glu Leu Gly Leu Leu Asp Cys Val Ser Tyr Ile Thr
    450                 455                 460
Gly Ala Ser Gly Ser Thr Trp Ala Leu Ala Asn Leu Tyr Glu Asp Pro
465                 470                 475                 480
Glu Trp Ser Gln Lys Asp Leu Ala Gly Pro Thr Glu Leu Leu Lys Thr
                485                 490                 495
Gln Val Thr Lys Asn Lys Leu Gly Val Leu Ala Pro Ser Gln Leu Gln
            500                 505                 510
Arg Tyr Arg Gln Glu Leu Ala Glu Arg Ala Arg Leu Gly Tyr Pro Ser
        515                 520                 525
Cys Phe Thr Asn Leu Trp Ala Leu Ile Asn Glu Ala Leu Leu His Asp
    530                 535                 540
Glu Pro His Asp His Lys Leu Ser Asp Gln Arg Glu Ala Leu Ser His
545                 550                 555                 560
Gly Gln Asn Pro Leu Pro Ile Tyr Cys Ala Leu Asn Thr Lys Gly Gln
                565                 570                 575
Ser Leu Thr Thr Phe Glu Phe Gly Glu Trp Cys Glu Phe Ser Pro Tyr
            580                 585                 590
Glu Val Gly Phe Pro Lys Tyr Gly Ala Phe Ile Pro Ser Glu Leu Phe
        595                 600                 605
Gly Ser Glu Phe Phe Met Gly Gln Leu Met Lys Arg Leu Pro Glu Ser
    610                 615                 620
```

```
Arg Ile Cys Phe Leu Glu Gly Ile Trp Ser Asn Leu Tyr Ala Ala Asn
625                 630                 635                 640

Leu Gln Asp Ser Leu Tyr Trp Ala Ser Glu Pro Ser Gln Phe Trp Asp
            645                 650                 655

Arg Trp Val Arg Asn Gln Ala Asn Leu Asp Lys Glu Gln Val Pro Leu
                660                 665                 670

Leu Lys Ile Glu Glu Pro Pro Ser Thr Ala Gly Arg Ile Ala Glu Phe
            675                 680                 685

Phe Thr Asp Leu Leu Thr Trp Arg Pro Leu Ala Gln Ala Thr His Asn
690                 695                 700

Phe Leu Arg Gly Leu His Phe His Lys Asp Tyr Phe Gln His Pro His
705                 710                 715                 720

Phe Ser Thr Trp Lys Ala Thr Thr Leu Asp Gly Leu Pro Asn Gln Leu
                725                 730                 735

Thr Pro Ser Glu Pro His Leu Cys Leu Leu Asp Val Gly Tyr Leu Ile
                740                 745                 750

Asn Thr Ser Cys Leu Pro Leu Leu Gln Pro Thr Arg Asp Val Asp Leu
            755                 760                 765

Ile Leu Ser Leu Asp Tyr Asn Leu His Gly Ala Phe Gln Gln Leu Gln
770                 775                 780

Leu Leu Gly Arg Phe Cys Gln Glu Gln Gly Ile Pro Phe Pro Pro Ile
785                 790                 795                 800

Ser Pro Ser Pro Glu Glu Gln Leu Gln Pro Arg Glu Cys His Thr Phe
                805                 810                 815

Ser Asp Pro Thr Cys Pro Gly Ala Pro Ala Val Leu His Phe Pro Leu
                820                 825                 830

Val Ser Asp Ser Phe Arg Glu Tyr Ser Ala Pro Gly Val Arg Arg Thr
                835                 840                 845

Pro Glu Glu Ala Ala Ala Gly Glu Val Asn Leu Ser Ser Asp Ser
850                 855                 860

Pro Tyr His Tyr Thr Lys Val Thr Tyr Ser Gln Glu Asp Val Asp Lys
865                 870                 875                 880

Leu Leu His Leu Thr His Tyr Asn Val Cys Asn Asn Gln Glu Gln Leu
                885                 890                 895

Leu Glu Ala Leu Arg Gln Ala Val Gln Arg Arg Gln Arg Arg Pro
                900                 905                 910

His
```

(2) INFORMATION FOR SEQ ID NO:4:

(i) SEQUENCE CHARACTERISTICS:
        (A) LENGTH: 3085 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:4:

```
CCGUGACCCC AGAUGGUUAC GCGGAUGCCG UGAGAGGGGA UCGCUUCAUG AUGCCAGCUG     60

AGCGCCGCCU GCCCCUGAGC UUCGUGCUGG AUGUGCUGGA GGGCCGGGCC CAGCACCCUG    120

GAGUCCUCUA UGUGCAGAAG CAGUGCUCCA ACCUGCCCAG CGAGCUGCCC CAGCUGCUGC    180

CUGAUCUGGA AUCCCAUGUG CCCUGGGCCU CCGAAGCCCU GGGAAAGAUG CCCGAUGCUG    240

UGAACUUCUG GCUGGGGGAG GCGGCUGCAG UGACUUCUUU GCACAAGGAC CACUAUGAGA    300
```

```
ACCUCUACUG CGUGGUCUCA GGAGAGAAGC AUUUCCUGUU CCAUCCGCCC AGCGACCGGC    360

CCUUCAUCCC CUAUGAGCUG UACACGCCGG CAACCUACCA GCUAACUGAA GAGGGCACCU    420

UUAAGGUGGU GGAUGAAGAG GCCAUGGAGA AGGCAGAGGU GUCCAGGACC UGCCUGCUCA    480

CGGUUCGUGU CCUGCAGGCC CAUCGCCUAC CCUCUAAGGA CCUAGUGACC CCCUCUGACU    540

GCUACGUGAC UCUCUGGCUG CCCACGGCCU GCAGCCACAG GCUCCAGACA CGCACGGUCA    600

AGAACAGCAG UAGCUCUGUC UGGAACCAGA GCUUUCACUU CAGGAUCCAC AGGCAGCUCA    660

AGAAUGUCAU GGAACUGAAA GUCUUUGACC AGGACCUGGU GACCGGAGAU GACCCUGUGU    720

UGUCAGUACU GUUUGAUGCG GGGACUCUGC GGGCUGGGGA GUUCCGGCGC GAGAGCUUCU    780

CACUGAGCCC UCAGGGUGAG GGGCGCCUGG AAGUUGAAUU UGCCCUGCAG AGUCUGGCUG    840

ACCGUGGCGA GUGGCUCGUC AGCAAUGGCG UUCUGGUGGC CCGGGAGCUC UCCUGCUUGC    900

ACGUUCAACU GGAGGAGACA GGAGACCAGA AGUCCUCAGA GCACAGAGUU CAGCUUGUGG    960

UUCCUGGGUC CUGUGAGGGU CCGCAGGAGG CCUCUGUGGG CACUGGCACC UUCCGCUUCC   1020

ACUGCCCAGC CUGCUGGGAG CAGGAGCUGA GUAUUCGCCU GCAGGAUGCC CCCGAGGAGC   1080

AACUAAAGGC GCCACUGAGU GCCCUGCCCU CUGGUCAAGU GGUGAGGCUU GUCUUCCCCA   1140

CGUCCCAGGA GCCCCUGAUG AGAGUGGAGC UGAAAAAAGA AGCAGGACUG AGGGAGCUGG   1200

CCGUGCGACU GGGCUUCGGG CCCUGUGCAG AGGAGCAGGC CUUCCUGAGC AGGAGGAAGC   1260

AGGUGGUGGC CGCGGCCUUG AGGCAGGCCC UGCAGCUGGA UGGAGACCUG CAGGAGGAUG   1320

AGAUCCCAGU GGUAGCUAUU AUGGCCACUG GUGGUGGGAU CCGGGCAAUG ACUUCCCUGU   1380

AUGGGCAGCU GGCUGGCCUG AAGGAGCUGG GCCUCUUGGA UUGCGUCUCC UACAUCACCG   1440

GGGCCUCGGG CUCCACCUGG GCCUUGGCCA ACCUUUAUGA GGACCCAGAG UGGUCUCAGA   1500

AGGACCUGGC AGGGCCCACU GAGUUGCUGA AGACCCAGGU GACCAAGAAC AAGCUGGGUG   1560

UGCUGGCCCC CAGCCAGCUG CAGCGGUACC GGCAGGAGCU GGCCGAGCGU GCCCGCUUGG   1620

GCUACCCAAG CUGCUUCACC AACCUGUGGG CCCUCAUCAA CGAGGCGCUG CUGCAUGAUG   1680

AGCCCCAUGA UCACAAGCUC UCAGAUCAAC GGGAGGCCCU GAGUCAUGGC CAGAACCCUC   1740

UGCCCAUCUA CUGUGCCCUC AACACCAAAG GCAGAGCCU GACCACUUUU GAAUUUGGGG   1800

AGUGGUGCGA GUUCUCUCCC UACGAGGUCG GCUUCCCCAA GUACGGGGCC UUCAUCCCCU   1860

CUGAGCUCUU UGGCUCCGAG UUCUUUAUGG GGCAGCUGAU GAAGAGGCUU CCUGAGUCCC   1920

GCAUCUGCUU CUUAGAAGGU AUCUGGAGCA ACCUGUAUGC AGCCAACCUC CAGGACAGCU   1980

UAUACUGGGC CUCAGAGCCC AGCCAGUUCU GGGACCGCUG GGUCAGGAAC CAGGCCAACC   2040

UGGACAAGGA GCAGGUCCCC CUUCUGAAGA UAGAAGAACC ACCCUCAACA GCCGGCAGAA   2100

UAGCUGAGUU UUUCACCGAU CUUCUGACGU GGCGUCCACU GGCCCAGGCC ACACAUAAUU   2160

UCCUGCGUGG CCUCCAUUUC CACAAAGACU ACUUCAGCA UCCUCACUUC UCCACAUGGA   2220

AAGCUACCAC UCUGGAUGGG CUCCCCAACC AGCUGACACC CUCGGAGCCC CACCUGUGCC   2280

UGCUGGAUGU UGGCUACCUC AUCAAUACCA GCUGCCUGCC CUCCUGCAG CCCACUCGGG   2340

ACGUGGACCU CAUCCUGUCA UUGGACUACA ACCUCCACGG AGCCUUCCAG CAGUUGCAGC   2400

UCCUGGGCCG GUUCUGCCAG GAGCAGGGGA UCCCGUUCCC ACCCAUCUCG CCCAGCCCCG   2460

AAGAGCAGCU CCAGCCUCGG GAGUGCCACC ACCUCUCCGA CCCACCUCGC CCGGAGCCC   2520

CUGCGGUGCU GCACUUCCU CUGGUCACGC ACUCCUUCCG GGACUACCUCG GCCCUGGGGG   2580

UCCGGCGGAC ACCCGAGGAG GCGGCAGCUG GGAGGUGAA CCUGUCUUCA UCGGACUCUC   2640
```

-continued

```
CCUACCACUA CACGAAGGUG ACCUACAGCC AGGAGGACGU GGACAAGCUG CUGCACCUGA   2700

CACAUUACAA UGUCUGCAAC AACCAGGAGC AGCUGCUGGA GGCUCUGCGC CAGGCAGUGC   2760

AGCGGAGGCG GCAGCGCAGG CCCCACUGAU GGCCGGGGCC CCUGCCACCC CUAACUCUCA   2820

UUCAUUCCCU GGCUGCUGAG UUGCAGGUGG GAACUGUCAU CACGCAGUGC UUCAGAGCCU   2880

CGGGCUCAGG UGGCACUGUC CCAGGGUCCA GGCUGAGGGC UGGGAGCUCC CUUGCGCCUC   2940

AGCAGUUUGC AGUGGGGUAA GGAGGCCAAG CCCAUUUGUG UAAUCACCCA AAACCCCCCG   3000

GCCUGUGCCU GUUUUCCCUU CUGCGCUACC UUGAGUAGUU GGAGCACUUG AUACAUCACA   3060

GACUCAUACA AAAAAAAAAA AAAAA                                         3085
```